United States Patent
Tsuji et al.

(10) Patent No.: US 7,604,406 B2
(45) Date of Patent: Oct. 20, 2009

(54) MICROCHIP AND ANALYZING METHOD AND DEVICE EMPLOYING IT

(75) Inventors: Kouichi Tsuji, Osaka (JP); Takehiko Kitamori, Tokyo (JP); Manabu Tokeshi, Kanagawa (JP); Keita Tanaka, Osaka (JP); Kazuhiko Nakano, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/064,456

(22) PCT Filed: Aug. 30, 2006

(86) PCT No.: PCT/JP2006/317078

§ 371 (c)(1),
(2), (4) Date: Jun. 25, 2008

(87) PCT Pub. No.: WO2007/026750

PCT Pub. Date: Mar. 8, 2007

(65) Prior Publication Data

US 2009/0147912 A1    Jun. 11, 2009

(30) Foreign Application Priority Data

Sep. 1, 2005 (JP) ............... 2005-254037
Sep. 2, 2005 (JP) ............... 2005-254240

(51) Int. Cl.
*H05G 1/00* (2006.01)
(52) U.S. Cl. ............... 378/208; 378/79; 378/47
(58) Field of Classification Search ............ 378/44–50, 378/70, 79, 84, 204, 207, 208
See application file for complete search history.

(56) References Cited

U.S. PATENT DOCUMENTS 5,812,631 A    9/1998    Yan et al.

FOREIGN PATENT DOCUMENTS

| JP | 07-229862 A | 8/1995 |
| JP | 2002-022684 A | 1/2002 |
| JP | 2003-202306 A | 7/2003 |
| WO | WO-2004/051234 A1 | 6/2004 |

OTHER PUBLICATIONS

International Preliminary Examination Report for the Application No. PCT/JP2006/317078 dated Nov. 13, 2007.
International Search Report for the Application No. PCT/JP2006/317078 mailed Nov. 21, 2006.
Tsuji, Kouichi et al., "Grazing-Exit and Micro X-ray Fluorescence Analyses for Chemical Microchips", Analytical Sciences, Jul. 2005, vol. 21, pp. 799-803.
Claes, Martine et al., "Optimization of Sample Preparation for Grazing Emission X-ray Fluorescence in Micro- and Trace Analysis Applications", Spectrochimica Acta Part B 52, 1997, pp. 1064-1070.

*Primary Examiner*—Courtney Thomas
(74) *Attorney, Agent, or Firm*—Cheng Law Group, PLLC

(57) ABSTRACT

A plurality of elements can be analyzed simultaneously with high sensitivity using a microchip. The microchip (1) comprises a substrate (30), a channel (23) formed in the substrate (30), and an analyzing part (10) consisting of a part of flat surface of the substrate (30), where the outlet of the channel (23) is formed as an opening (9c) and measurement object liquid overflowed from the opening (9c) stays on the flat surface of the substrate (30) to become a sample of analysis. The measurement object liquid is made to overflow as a sample of analysis to the analyzing part (10) using the microchip (1) and then the sample of analysis is preferably dried before a primary X-ray is made to enter under conditions of total reflection and fluorescent X-rays are detected.

13 Claims, 18 Drawing Sheets

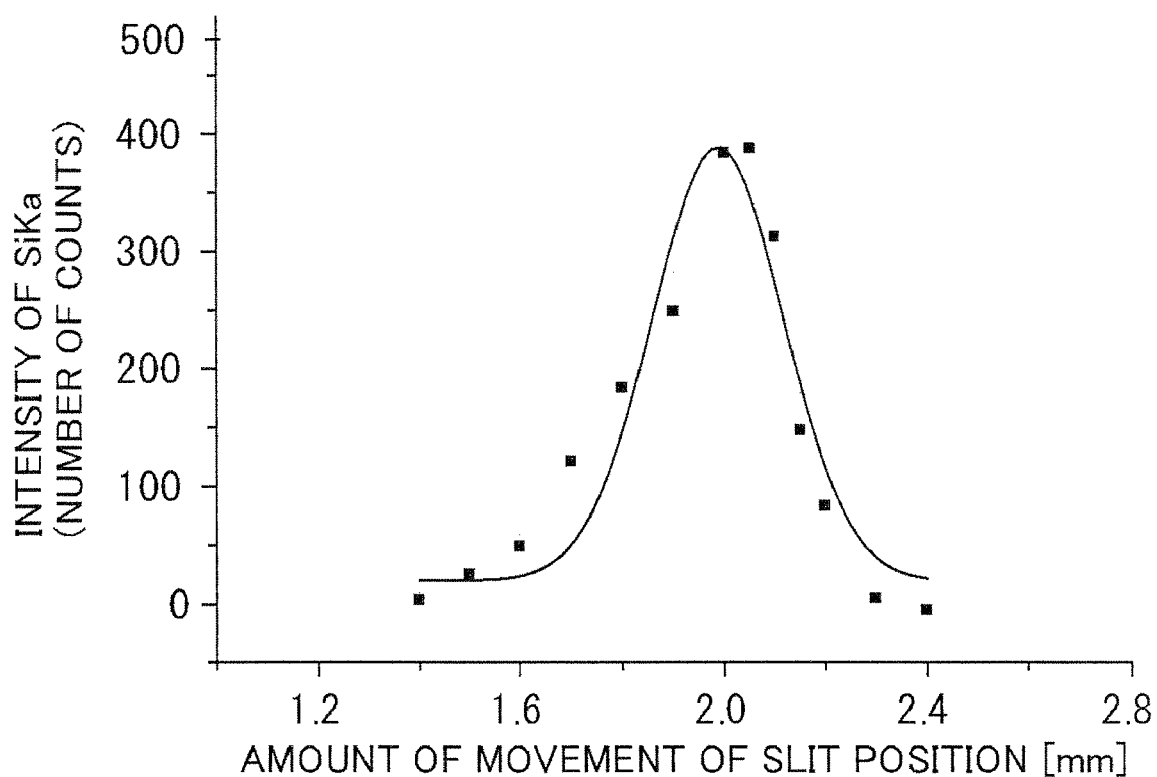

MICROCHIP AND ANALYZING METHOD AND DEVICE EMPLOYING IT

FIELD OF THE ART

The present invention relates to a microchip having a channel formed in a substrate as well as to a method and a device for performing analysis using it.

BACKGROUND ART

In recent years, in the field of analytical chemistry, research of μTAS (Micro Total Analysis Systems) are becoming more and more prevalent. A microchip performs various chemical processes such as mixing, chemical reaction, separation and extraction in a minute channel formed, for example, in a chip of several centimeters square. When a chemical process is carried out in a micro size, the interfacial area per unit area where the chemical reaction takes place is larger as compared with the case of performing the chemical reaction in a macro size, so that scale reduction of a chemical apparatus, high-speed processing, reduction of the amount of reagents and the amount of discarding thereof, reduction of the time and higher efficiency of measurement, effects of saving energy, and the like are expected.

A sample solution processed by a microchip has been so far detected by the visible and ultraviolet ray absorption method, the laser spectroscopy method, or the like.

However, these methods are not those in which a plurality of elements are subjected to simultaneous elemental quantification, so that it has been difficult to perform minute analysis of a plurality of elements with a microchip.

On the other hand, as a method for quantitating a plurality of elements simultaneously, the fluorescent X-ray analyzing methods are known. Among these, the total reflection fluorescent X-ray analyzing method by which a primary X-ray is made to enter a sample under conditions of total reflection can measure the fluorescent X-ray coming from the sample surface or the impurities located thereon with a high sensitivity. The total reflection fluorescent X-ray analyzing method provides an advantage in that the angle of entering of the primary X-ray is minute, so that the reflected X-ray or the scattered X-ray hardly enters an X-ray detector, so that the continuous X-ray background noise is smaller as compared with an output level of the fluorescent X-ray detected by an X-ray detector, thereby enhancing the S/B (signal/background) ratio (See Patent Document 1).

Patent Document 1: Japanese Patent Application Laid-Open (JP-A) No. 2003-202306

Non-patent Document 1: M. Claes, P. de Bokx, N. Willard, P. Veny, R. Van Grieken, Spectrochim. Acta part B, 52 (1997) 1063-1070.)

DISCLOSURE OF THE INVENTION

Problems to be Solved by the Invention

However, the total reflection fluorescent X-ray analyzing method aims at making a primary X-ray be totally reflected on a flat solid surface, so that an X-ray cannot be radiated into a sample flowing through a microchannel at a minute angle of entering that satisfies the total reflection conditions. Therefore, there has never been a concept that the total reflection fluorescent X-ray analyzing method is used for detection in a microchip.

Therefore, an object of the present invention is to provide an analyzing method and an apparatus using a microchip as a method for analyzing a plurality of elements simultaneously with a high sensitivity.

Means for Solving the Problems

A microchip of the present invention includes a substrate; a channel formed in the substrate; and an analyzing part consisting of a partial region of a flat surface of the substrate and including an outlet of the channel, wherein the outlet is formed as an opening, and a measurement object liquid overflowing from the opening stays on the flat surface of the substrate to become a sample of analysis.

The measurement object liquid overflowed from the opening, when dried at the analyzing part, preferably forms a uniform dried trace with good reproducibility. One preferable mode of the analyzing part therefore is one in which the analyzing part is subjected to a surface treatment having affinity to the measurement object liquid. Another preferable mode of the analyzing part is one in which a region surrounding the analyzing part is subjected to a surface treatment having a water-repellent property to the measurement object liquid.

One preferable example of the analyzing part is one in which a primary X-ray is made to enter under conditions of total reflection, and a fluorescent X-ray generated from the sample of analysis located on the analyzing part is detected with an X-ray detector separately provided.

In order for the primary X-ray to provoke total reflection within the analyzing part on the microchip surface, there is a need such that no undulations are present at a position in the analyzing part where the primary X-ray enters. For this reason, it is preferable that the outlet from which the measurement object liquid overflows is disposed at a position offset from a center of the region forming the analyzing part.

An analyzing method of the present invention uses this microchip and includes the following steps (A) to (C):

(A) step of making the measurement object liquid overflow as a sample of analysis from the channel through the opening to the analyzing part by using this microchip;

(B) step of making a primary X-ray enter the sample of analysis overflowed to the analyzing part so as to achieve conditions of total reflection relative to a surface of the microchip; and (C) step of detecting a fluorescent X-ray generating from the sample of analysis.

In the event that the sample of analysis is an aqueous solution, since water absorbs an X-ray, the S/B ratio will become small when the X-ray is absorbed into the liquid sample, so that the analyzing method preferably includes a step of drying the sample of analysis on the analyzing part between the steps (A) and (B).

The channel performs, for example, liquid-supplying, chemical reaction, or separation.

It is preferable that the primary X-ray radiated onto the sample of analysis is condensed with use of a polycapillary X-ray lens in the step (B).

Further, so that almost all of the primary X-ray radiated onto the sample of analysis satisfies the conditions of total reflection, it is preferable to make the primary X-ray exiting from the polycapillary X-ray lens be in such a way that a cross-sectional shape in a direction perpendicular to a propagation direction is a linear shape parallel to the microchip surface.

It is preferable that the method shields against a primary X-ray part having an angle of entering that does not satisfy the conditions of total reflection relative to the microchip surface among the primary X-rays radiated onto the sample of analysis.

It is preferable that a polycapillary X-ray lens is disposed also on a side of the detector that detects the fluorescent X-ray so as to detect only the fluorescent X-ray coming from a minute region of the sample of analysis.

A microchip analyzing device of the present invention uses this microchip as a medium of measurement and includes a sample mounting base for mounting the microchip; an X-ray source for generating a primary X-ray; a primary X-ray entering adjustment mechanism for making the primary X-ray enter the analyzing part of the microchip under conditions of total reflection; and an X-ray detector disposed opposite to the analyzing part of the microchip for detecting a fluorescent X-ray generating from a sample of analysis on the analyzing part.

It is preferable that the primary X-ray entering adjustment mechanism includes a polycapillary X-ray lens for condensing and radiating the primary X-ray onto the microchip mounted on the sample mounting base. A polycapillary X-ray lens is a bundle of numerous fine glass tubes (monocapillaries) through which the X-ray propagates by total reflection, and is formed in such a manner that the track of the X-ray is bent by moderately bending the capillaries, and the X-rays exiting from the capillaries are condensed towards one point. Each monocapillary has such a shape that an inner diameter thereof once enlarges from a base end on a photoreceptive part side to a tip end on a radiation side and then gradually narrows toward the tip end. The polycapillary X-ray lens bends the track of the X-ray by the total reflection, and does not accompany spectroscopy, so that there is no damping of the X-ray intensity such as seen in the spectroscopy element using a spectroscopy crystal.

More preferably, in order to optimize the construction of the polycapillary X-ray lens so as to improve the precision of analysis and to achieve scale reduction of the X-ray emission source part, the cross-sectional shape in the direction perpendicular to the propagation direction of the primary X-ray exiting from the polycapillary X-ray lens is made to have a linear shape parallel to the surface of the microchip mounted on the sample mounting base. In order to achieve this, the polycapillary X-ray lens is such that end parts of the monocapillaries on the plane of entering opposite to the X-ray emission source are arranged in a circular plane shape, and end parts of the monocapillaries on the plane of exiting opposite to the sample are arranged to have a linear shape parallel to the surface of the microchip mounted on the sample mounting base so that radiation directions may be condensed towards one point. The analyzing part of the microchip is disposed at the position of the focal point thereof.

Further, in a more preferable mode, the primary X-ray entering adjustment mechanism includes a slit between an exiting side of the polycapillary X-ray lens and the sample mounting base, wherein the slit is disposed to shield against the primary X-ray having an angle of entering that does not satisfy the conditions of total reflection relative to the surface of the microchip mounted on the sample mounting base.

Here, the term "slit" generally refers to an elongate opening. However, in the present invention, it is sufficient that the slit can shield against the primary X-ray having an angle of entering that does not satisfy the conditions of total reflection, namely, the primary X-ray having an angle of entering larger than the critical angle of total reflection, so that the term is used as a concept that includes a shielding plate that only shields against the primary X-ray on the angle-of-entering side larger than the critical angle of total reflection, in addition to the elongate opening.

In the event that the slit shields against the X-rays having an angle other than the angle that suits the measurement, the X-ray intensity will be extremely weak and the fluorescent light will be minute and weak when too much shielding is carried out. When an excessively large X-ray source is used in order to compensate for the weakening of the X-ray intensity, the analyzing device will be large. On the other hand, when the slit is widened and the X-ray is radiated onto the microchip at a wide angle, the primary X-ray and the fluorescent X-ray coming from the parts other than the analyzing part to be measured will come out as a noise, thereby decreasing the precision of analysis.

Therefore, in a preferable mode in which the cross-sectional shape in the direction perpendicular to the propagation direction of the primary X-ray exiting from the polycapillary X-ray lens is made to have a linear shape parallel to the microchip surface of the analyzing part, the slit may not be disposed so as to avoid the problem of weakening of the X-ray intensity caused by the slit if the X-rays having an angle other than the angle that suits the measurement can be prevented from exiting even without the use of a slit. Even if a slit is used, the ratio of the X-ray that is shut out by the slit will be small by condensing the X-rays in a linear shape along the shape of the slit. In this mode, irrespective of the presence or absence of the slit, the problem of weakening of the X-ray intensity to a large extent can be avoided, thereby eliminating the need for the use of an excessively large X-ray source.

The sample mounting base preferably includes an adjustment mechanism for adjusting directions in a horizontal plane, a height direction, and an inclination direction relative to an entering X-ray, of the surface of the microchip mounted thereon.

Also, it is preferable that the microchip analyzing device includes a polycapillary X-ray lens between the microchip mounted on the sample mounting base and the detector so as to detect only the fluorescent X-ray coming from a minute region within the analyzing part.

EFFECTS OF THE INVENTION

So far, there has not been one in which a plurality of elements are detected simultaneously in an analysis using a microchip. However, according to the analyzing method using the microchip of the present invention, the total reflection fluorescent X-ray analyzing method can be applied to the detection, so that a plurality of elements can be simultaneously analyzed in a non-destructive manner and moreover under atmospheric pressure and at a high sensitivity.

When the sample of analysis of the analyzing part is dried, the S/B ratio of the fluorescent X-ray will be improved, and the measurement sensitivity will be improved.

Also, the total reflection fluorescent X-ray analysis device can be reduced in scale, and also has good compatibility with a microchip which is originally small, so that an analyzing system portable as a whole can be constructed.

An ordinary total reflection fluorescent X-ray analysis is such that a primary X-ray radiates a wide range without being spatially condensed. However, when a polycapillary X-ray lens is used, the primary X-ray can be condensed to a minute measurement site without reducing the intensity of the primary X-ray. In this manner, the so-called X-ray focusing effect can be obtained while satisfying the conditions of total reflection on the microchip surface, so that the fluorescent X-ray intensity will increase, and the measurement sensitivity will be improved.

When it is constructed in such a manner that the slit shields against the primary X-ray having an angle of entering that does not satisfy the conditions of total reflection relative to the microchip surface, the angle of entering of all of the primary X-rays relative to the sample surface can be kept below the critical angle of the total reflection, whereby the background can be further reduced to improve the measurement limits.

Further, when the cross-sectional shape in the direction perpendicular to the propagation direction of the primary X-ray exiting from the polycapillary X-ray lens is made to have a linear shape parallel to the microchip surface, the angle of entering of the primary X-ray relative to the sample surface can be kept below the critical angle of total reflection even if the slit is not provided. Therefore, almost all of the X-ray that has been captured into the polycapillary X-ray lens from the X-ray source will be radiated onto the analyzing part on the microchip surface. Further, the uniformity of the angle is high, and the total reflection conditions are gathered together, so that the precision of analysis will be extremely high, and the device will be suitable for microanalysis. Also, the X-ray source can be relatively reduced in scale, thereby enabling a device suitable for convenient carriage.

Even in the case in which the cross-sectional shape in the direction perpendicular to the propagation direction of the primary X-ray exiting from the polycapillary X-ray lens is made to have a linear shape parallel to the microchip surface, the precision will be further raised when a slit is added.

When a polycapillary X-ray lens is provided also between the sample and the detector, one will be able to detect only the fluorescent X-ray coming from the minute region on the sample surface.

BRIEF DESCRIPTION OF THE DRAWINGS

FIG. 12 is a graph showing a relationship between an amount of movement of the slit in the up-and-down direction and an intensity of a SiKα line, which is a fluorescent X-ray from a silicon wafer, in the analyzing device of the embodiment.

Figure 1A:
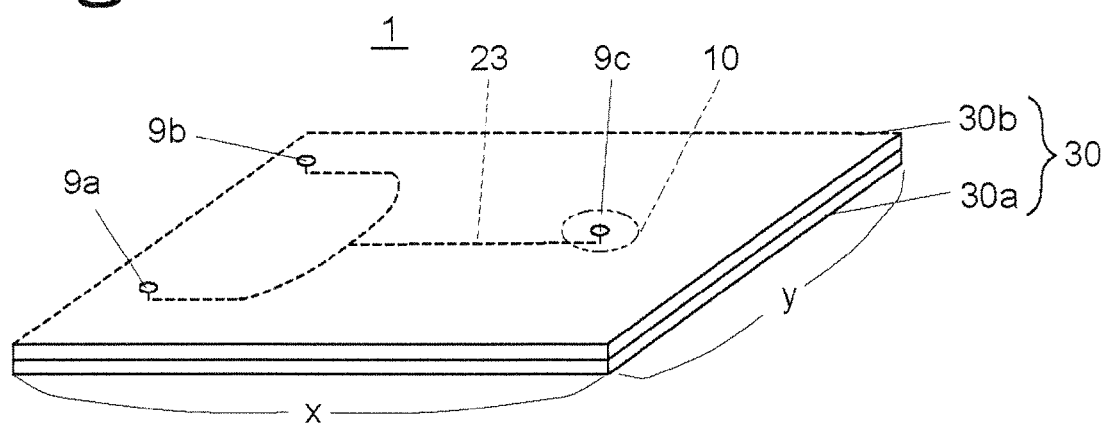
FIG. 1A is a perspective view showing one embodiment of a microchip.

DESCRIPTION OF THE SYMBOLS 1 microchip
2 X-ray radiating part
3 X-ray source
5 reflection plate
7, 7a, 7b slit
9a, 9b liquid inlet
9c liquid outlet
10, 10a analyzing part
11 detector
13 sample mounting base
13a stepping motor
13b inclination motor
21 microsyringe
23 channel
30a, 30b substrate
36 channel cross-section
35, 45, 55, 65 polycapillary X-ray lens
35a, 45a, 55a, 65a plane of entering
35c, 45c, 55 monocapillary
45b, 55b, 65b plane of exiting

BEST MODES FOR IMPLEMENTING THE INVENTION

Hereinafter, one embodiment of the present invention will be described.

Figure 1B:
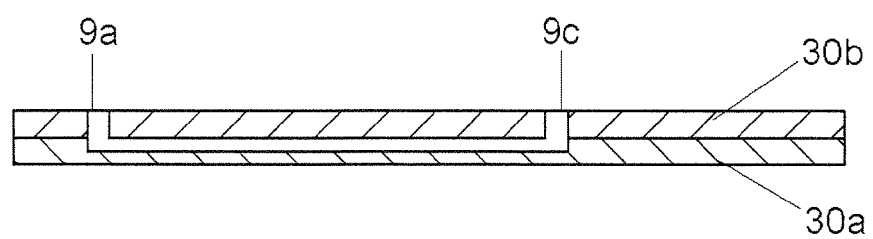
FIG. 1B is a cross-sectional view of the embodiment along a channel from a liquid inlet 9a to a liquid outlet 9b.
Figure 1C:
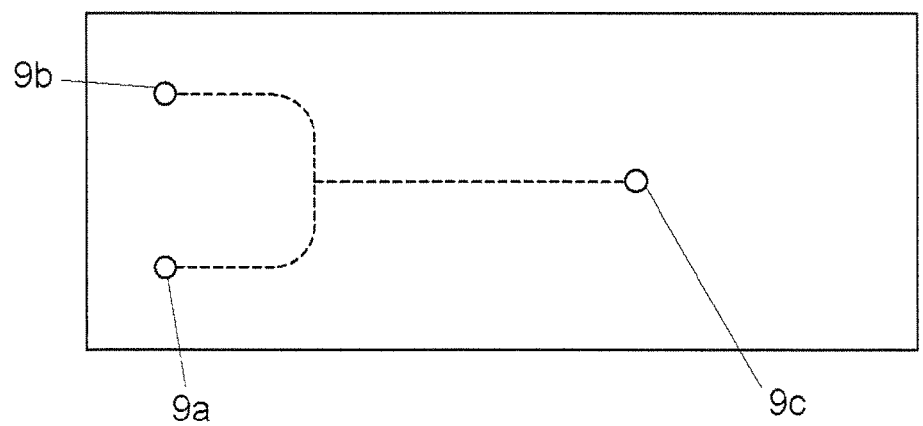
FIG. 1C is a top view of the embodiment.
Figure 1D:
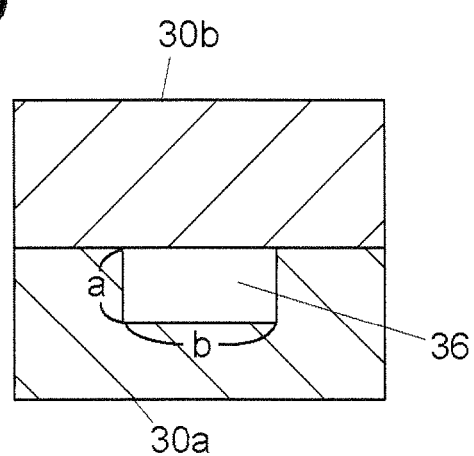
FIG. 1D is a cross-sectional view of a microchannel of the embodiment.

FIGS. 1A to 1D are one embodiment of a microchip, wherein FIG. 1A is a perspective view; FIG. 1B is a cross-sectional view along a channel from a liquid inlet 9a to a liquid outlet 9c; FIG. 1C is a top view; and FIG. 1D is one example of the cross-sectional view of a micro channel.

The microchip 1 includes a substrate 30, a channel 23 formed in the substrate 30, and an analyzing part 10 consisting of a partial region of a flat surface of the substrate 30 and including an outlet of the channel, where the outlet is formed as an opening 9c, and a measurement object liquid overflowed from the opening 9c stays on the flat surface of the substrate 30 to become a sample of analysis.

The substrate 30 is formed by bonding two sheets of flat substrates 30a, 30b. In one substrate 30a, a groove 23 is formed to become the channel, and the other substrate 30b is bonded so as to cover the groove 23. Through-holes 9a to 9c are opened in the substrate 30b at a position of end parts of the channel 23. When the substrates 30a, 30b are bonded to become the microchip 1, the holes 9a to 9c appear as openings on the flat surface of the substrate 30b. The holes 9a, 9b are liquid inlets of reaction liquid or the like, and the hole 9c is a liquid outlet.

The size of the microchip 1 is, for example, longitudinally x=70 mm and transversely y=30 mm, and the thickness of the substrates 30a, 30b is 0.7 mm respectively. A cross-section 36 of the channel 23 is, for example, such that the depth a=40 μm, and the width b=100 μm. The inner diameter of the through-holes 9a, 9b is 0.5 mm, and the inner diameter of the through-hole 9c is 0.2 mm. However, the shape and the size of the microchip and the channel of the present invention are not limited to the above-described ones.

Figure 2:
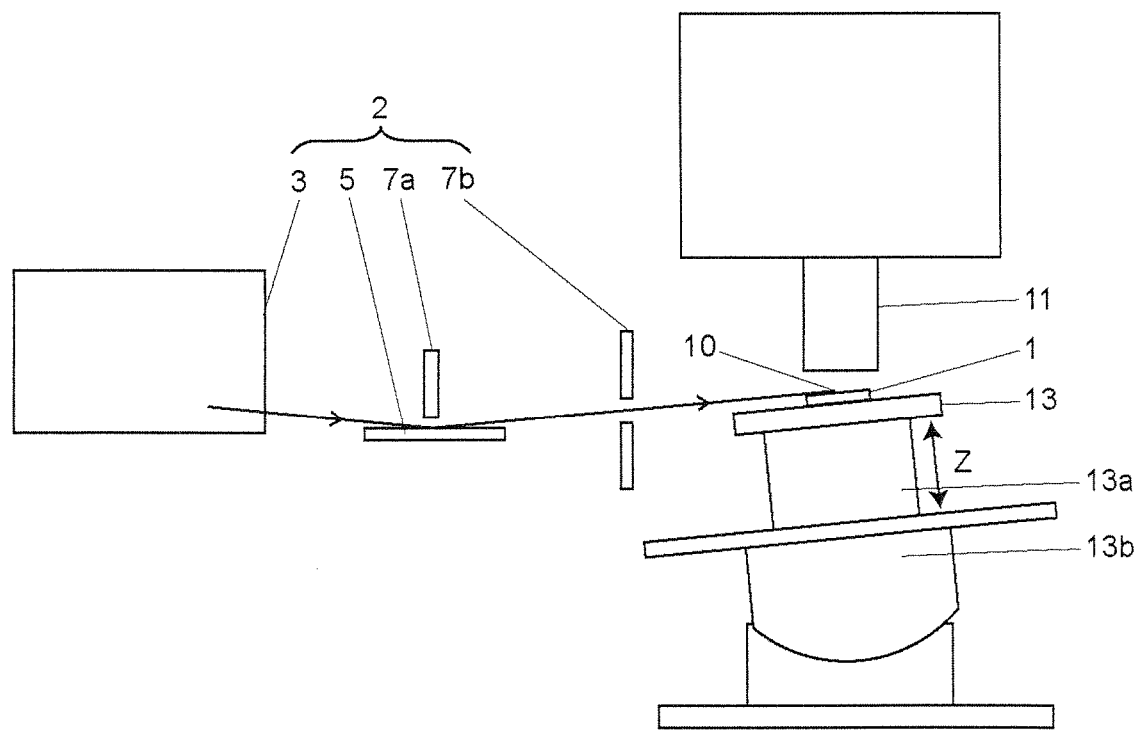
FIG. 2 is a schematic front view showing one embodiment of an analyzing device.

FIG. 2 is a schematic front view of an analyzing device using this microchip.

A sample mounting base 13 is for mounting the microchip 1. A primary X-ray radiating part 2 is provided that makes a primary X-ray enter an analyzing part on the surface of the microchip 1 mounted on the sample mounting base 13 at an angle of entering that provokes total reflection. The primary X-ray radiating part 2 includes an X-ray source 3 that generates an X-ray, a multiple-layer substrate 5 for making the X-ray monochromatic, and slits 7a, 7b for radiating onto a sample only the X-ray that has been made monochromatic. In order to detect a fluorescent X-ray generated from the sample on the analyzing part of the microchip 1, an X-ray detector 11 is disposed to oppose the analyzing part of the microchip 1 mounted on the sample mounting base 13.

The sample mounting base 13 includes adjustment mechanisms 13a, 13b, whereby with use of the adjustment mechanisms 13a, 13b, the height direction (Z-direction) of the surface of the microchip 1 mounted on the sample mounting base 13 and the inclination direction (θ) of the surface of the microchip 1 relative to the entering X-ray can be adjusted. The adjustment mechanisms 13a, 13b include a stepping motor 13a for performing adjustment of the height direction and an inclination motor 13b disposed under the stepping motor 13a for adjusting the inclination of the surface of the microchip 1 relative to the entering X-ray.

As an X-ray source 3, a commercially available X-ray tube is used, where an X-ray transmitting material such as beryllium, boron nitride, or graphite is used for the X-ray exiting window of the X-ray source 3. Between the X-ray exiting window of the X-ray source 3 and the multiple-layer substrate 5, there may be provided a suitable filter such as zirconium, aluminum, or brass in accordance with the elements to be measured so as to prevent the X-ray deriving from the tube bulb from affecting the fluorescent X-ray measurement. Here, as the X-ray source 3, an X-ray tube was used having molybdenum as a target and having a beryllium X-ray exiting window. A zirconium filter was disposed between the X-ray exiting window of the X-ray source 3 and the multiple-layer substrate 5.

For the X-ray detector 11, one is provided with a wavelength dispersive spectrometer and another is provided with an energy dispersive X-ray spectrometer. The wavelength dispersive spectrometer uses a diffraction phenomenon of a crystal of warpage type. The energy dispersive X-ray spectrometer captures all the X-rays generated from the sample simultaneously into the detector, and performs energy selection of the X-rays in an electrical manner. The energy dispersive X-ray spectrometer has an advantage in that, though the energy dissolution performance is inferior to that of the wavelength dispersive spectrometer, the measurement time can be made short, and the whole energy range can be simultaneously measured. In contrast, the wavelength dispersive spectrometer has an advantage in that, though the measurement time is longer than that of the energy dispersive X-ray spectrometer, the energy dissolution performance is superior. In the element analysis, either one of these two kinds of spectrometers different in dissolution performance can be used, and also these may be used in combination. Here, in order to make the measurement time short, an energy dispersive X-ray spectrometer is used.

When a liquid sample overflowed to the analyzing part 10 of the microchip 1 is an aqueous solution, it is preferably dried and concentrated to form a solid sample so as to avoid absorption of the X-ray by water. The drying can be carried out by natural drying; however, the drying time will be short if one makes use of heating for forced drying. For that purpose, a heating mechanism may be provided in the sample mounting base 13.

Next, one example of a method for producing the microchip 1 will be described.

A quartz glass substrate is used as the substrates 30a, 30b. First, a photoresist is applied on one glass substrate 30a for prebaking, and the photoresist is exposed to a UV (ultraviolet) ray via a photomask. Thereafter, the photoresist is developed for patterning, and after postbaking, the substrate 30a is etched using the photoresist pattern as a mask, so as to form a groove that will be the channel 23. Thereafter, the photoresist is removed. The etching may be either one of dry etching and wet etching. For example, wet etching is carried out using an aqueous solution of hydrofluoric acid as an etching liquid. The through-holes 9a to 9c are opened through the other substrate 30b by the sand blast method or the like.

The two sheets of the substrates 30a, 30b in which the channel groove 23 and the though-holes 9a to 9c are formed in this manner are joined in a liquid-tight manner by heating and pressurizing after superposing the substrate 30b onto the surface of the substrate 30a in which the groove 23 is formed.

As a material of the substrates, other glass substrates, silicon substrates, and resin substrates in addition to the quartz glass substrates can be used. In any case, the groove becoming the channel and the through-holes can be formed by chemical or mechanical means, or by various means such as laser radiation or ion etching.

In this embodiment, a microchip made of quartz glass was fabricated. However, since quartz glass is inherently hydrophobic, it is preferable to perform a chemical treatment to make the surface of the channel be hydrophilic so as to facilitate handling of the aqueous solution sample, before joining the two sheets of the substrates.

One example of the hydrophilizing treatment will be shown in the order of steps.

(1) immersion into hydrochloric acid so as to dissolve and remove impurity metal components.

(2) washing with water.

(3) immersion into ethanol so as to link the aqueous solvent and the organic solvent.

(4) immersion into acetone so as to remove organic substances.

(5) immersion into ethanol so as to link the aqueous solvent and the organic solvent again.

(6) washing with water.

(7) immersion into an NaOH solution for about 30 minutes so as to modify the surface with an OH group.

(8) washing with water to wash NaOH away.

By passing through these steps, the channel formed in the microchip 1 will be hydrophilic.

Next, an operation of the present embodiment will be described.

Figure 3:
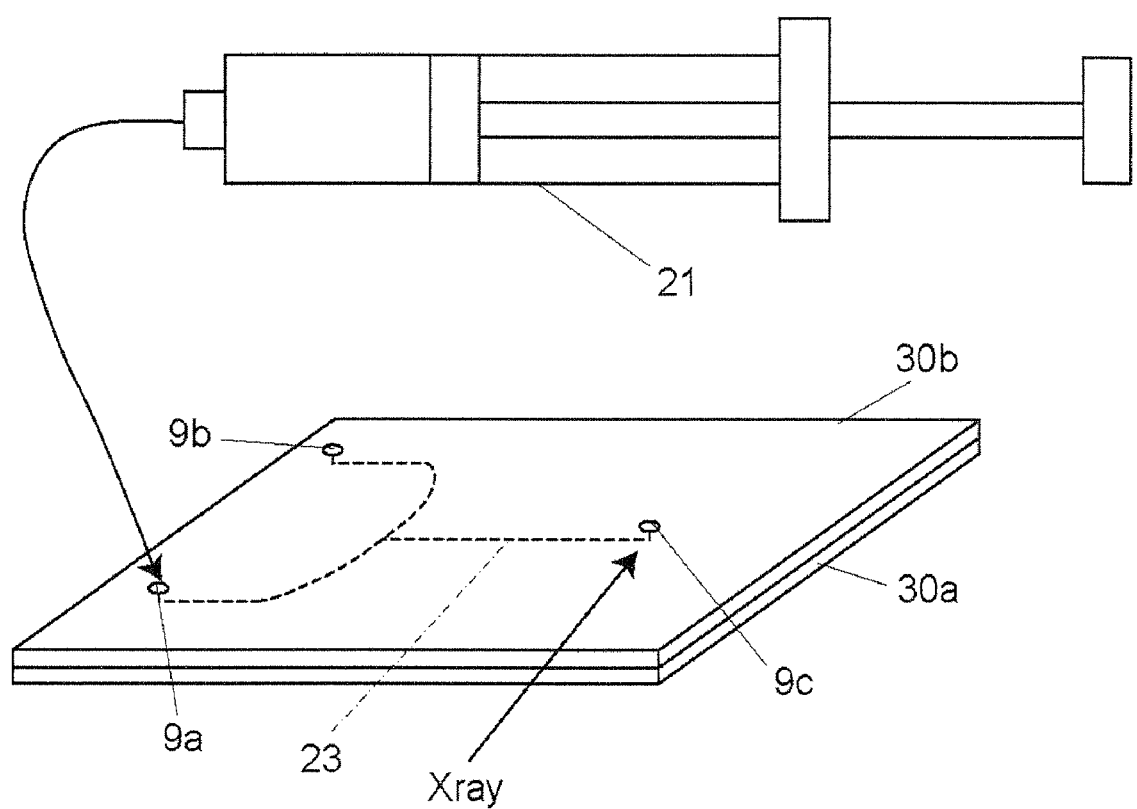
FIG. 3 is a schematic perspective view of an experiment operation when a sample solution is injected into a microchip and analyzed.

FIG. 3 is a schematic view of an experiment operation when a sample solution is injected into the microchip 1 to be analyzed. With use of a microsyringe 21, a reaction liquid is injected into the liquid inlet 9a of the microchip 1. In a similar manner, the other reaction liquid is injected into the liquid inlet 9b. The two reaction liquids will react in the channel 23, and pass from the channel 23 through the liquid outlet 9c to overflow and spread to the analyzing part on the substrate 30b.

Figure 4:
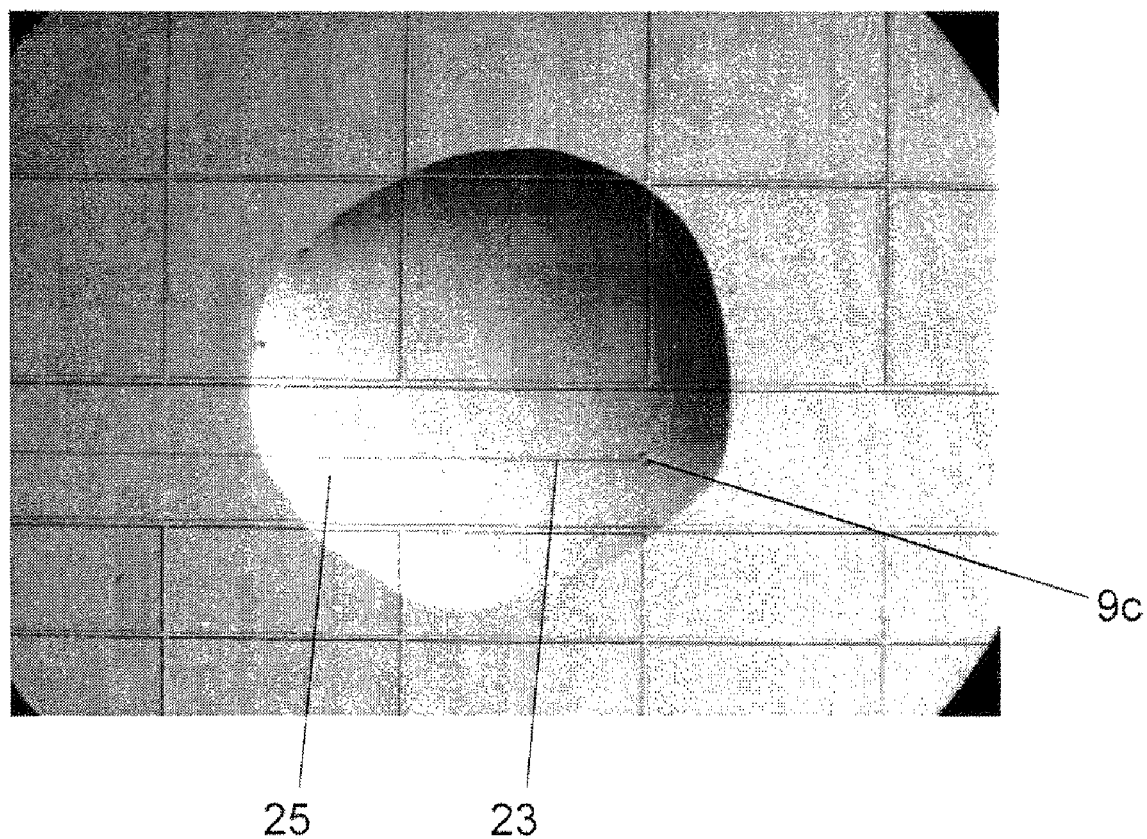
FIG. 4 is an image showing a state in which a liquid for sample having flowed out to an analyzing part is developed.

FIG. 4 is an image showing a state in which the overflowed solution has spread out to the surroundings of the liquid outlet 9e, where the region having an almost circular shape shown by the reference symbol 25 is the solution that has spread out to the analyzing part. The solvent of this solution sample is dried to be removed, and thereafter a primary X-ray is radiated under the conditions of total reflection so as to perform the element analysis of the sample by the total reflection fluorescent X-ray analyzing method.

Figure 5:
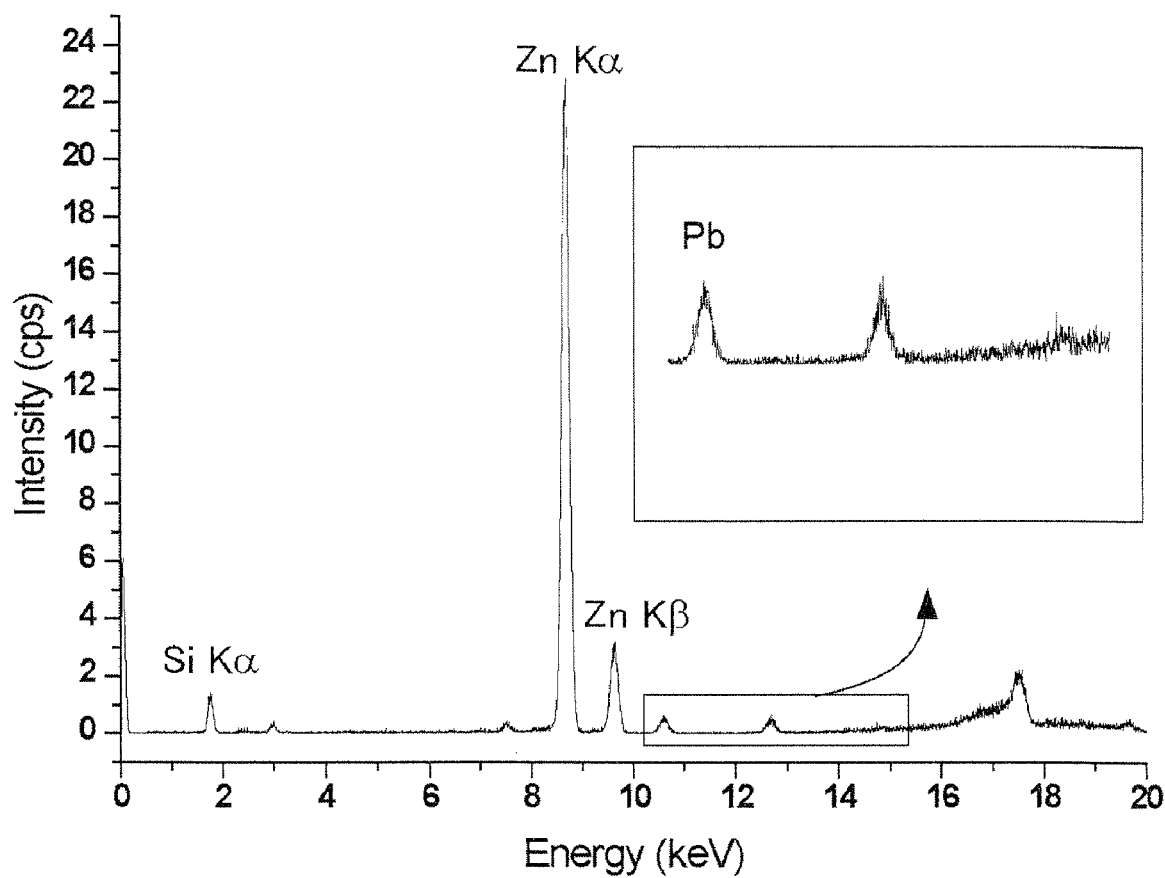
FIG. 5 is a fluorescent X-ray spectrum when a Zn standard sample is measured.

FIG. 5 shows one example of the fluorescent X-ray spectrum as measured with use of the microchip of this embodiment. In this case, the channel 23 is not used for reaction, but it is used only for passing of the sample solution. For this reason, it was used in a state in which one liquid inlet 9b is closed. As a sample solution, a Zn standard solution (1.017 mg/mL) was measured. With use of the syringe 21, 0.08 mL of the sample solution was supplied at a flow rate of 0.2 mL/h through the liquid inlet 9a, and was made to overflow to the analyzing part surrounding the liquid outlet 9c to be developed. After the developed sample solution was dried, total reflection fluorescent X-ray analysis was carried out. For the measurement, an Mo target of the X-ray source 3 was operated with 30 keV at 20 mA, and the fluorescent X-ray was detected for 60 seconds by an energy dispersive detector.

In the fluorescent X-ray spectrum of FIG. 5, the horizontal axis represents energy, and the vertical axis represents the fluorescent X-ray intensity (counts/second). Among the fluorescent X-rays within the range of 1 to 20 keV of energy, the part surrounded by the frame of 10 to 15 keV is shown enlarged in the upper right. The peak located around 1.8 keV represents the fluorescent X-ray generated from Si in the quarts glass which is the substrate of the microchip; the peaks located around 8.5 keV and 9.5 keV represent the fluorescent X-ray generated from Zn in the Zn standard sample; and the peak located around 10.5 keV represents the fluorescent X-ray generated from Pb wherein the lead plate used for shielding against the X-ray seems to be the generation source. The peak around 17.4 keV is an MoKa line which is the excitation X-ray. From this result, it has been observed that the noise is small in the signal as a whole, and the analyzing method using the microchip of the present invention has a good S/B ratio.

Figure 6:
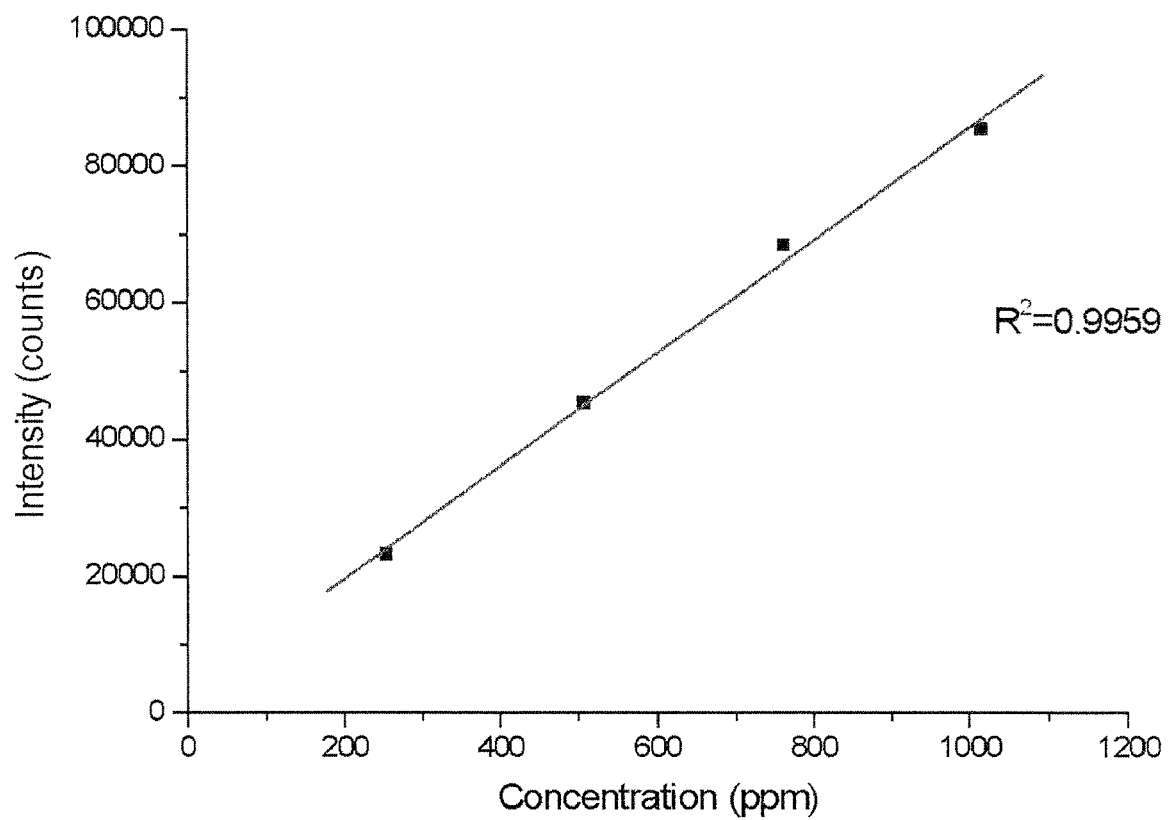
FIG. 6 is a graph showing a relationship between a fluorescent X-ray spectrum peak intensity and a concentration with respect to a standard sample.

FIG. 6 shows a relationship between the Zn concentration (ppm) and the intensity of the fluorescent X-ray spectrum peak of the ZnKα line (the integrated value of the number of counts of 60 seconds was regarded as the fluorescent X-ray intensity) for Zn standard samples prepared at four ion concentrations of Zn in the range of 0 to 1000 ppm. The weighted correlation coefficient $R^2$ was 0.9959, showing a good linearity. This shows that the data can be a calibration line in measuring the concentration of an unknown sample.

Figure 7:
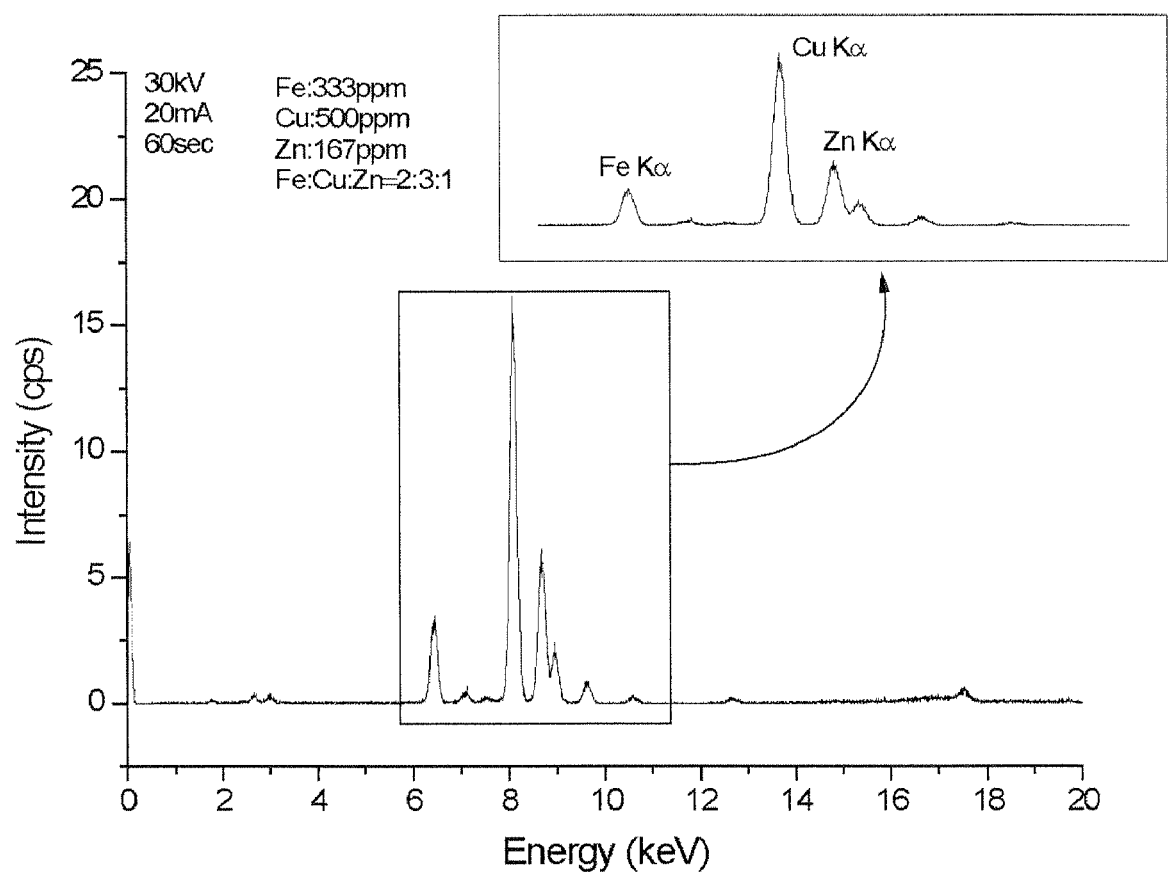
FIG. 7 is a fluorescent X-ray spectrum when a sample solution containing Fe, Cu, and Zn is measured.

FIG. 7 is a fluorescent X-ray spectrum when a sample solution containing Fe, Cu, and Zn was measured with use of the above-described microchip under the same conditions as in the measurement of the fluorescent X-ray spectrum shown in FIG. 5, to show that the simultaneous detection of a plurality of components is possible. The horizontal axis represents energy, and the vertical axis represents the detected X-ray intensity (counts/second). The sample solution has 330 ppm of Fe, 500 ppm of Cu, and 167 ppm of Zn, and the composition ratio is Fe:Cu:Zn=2:3:1.

Among the whole fluorescent X-ray spectra within the range of 1 to 20 keV of energy, the part surrounded by the frame of 6 to 11 keV is shown enlarged in the upper right. The peak located around 6.5 keV represents the fluorescent X-ray of Fe; the peak located around 8 keV represents the fluorescent X-ray of Cu; and the peak located around 9 keV represents the fluorescent X-ray of Zn. Since these peaks are distinctly separated from each other, it has been confirmed that a plurality of elements can be simultaneously quantitated.

Figure 8A:
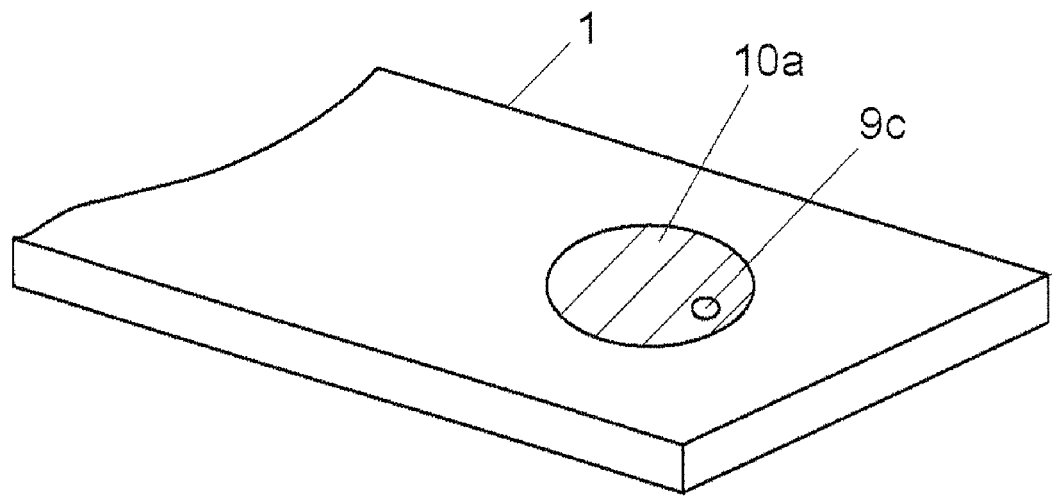
FIG. 8A is a partial perspective view showing another embodiment of a microchip.

FIG. 8A shows a neighborhood of the analyzing part of the microchip 1 of another embodiment. An analyzing part 10a has been subjected to a surface treatment that has affinity to the measurement object liquid. The shape of the analyzing part 10a is not particularly limited; however, a circular shape or an elliptic shape is preferable. The area of the analyzing part 10a is suitably 20 to 80 mm$^2$. As an example of the surface treatment having affinity to the analyzing part 10a, the following can be mentioned.

(1) In order to obtain a uniform dried trace on the region of the analyzing part 10a with good reproducibility, in the event that a polymer substrate such as a polycarbonate substrate is used as a material of the microchip, it is effective to perform an oxygen plasma treatment selectively on the analyzing part 10a. Specifically, for example, when a plasma surface treatment is carried out for 5 minutes with an output of 40 W in the presence of 20 Pascal of oxygen gas, the aqueous solution can be made to spread only to that region (See Non-patent Document 1).

(2) Similarly, as a method of reforming the property of the glass or polymer surface, a surfactant is applied on the analyzing part 10a.

(3) The analyzing part 10a is coated with a titanium oxide film.

Figure 8B:
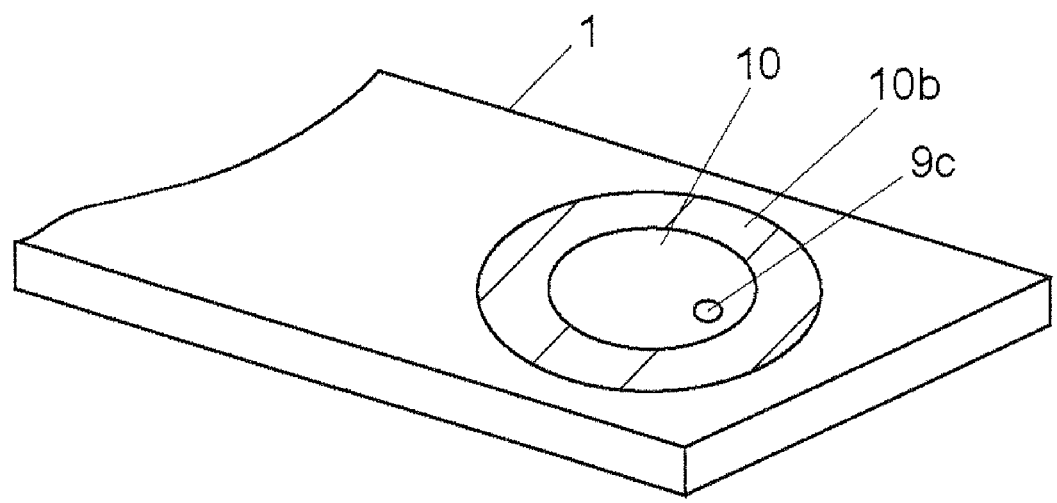
FIG. 8B is a partial perspective view showing still another embodiment of a microchip.

FIG. 8B shows a neighborhood of the analyzing part 10 of the microchip 1 of another embodiment. A region 10b surrounding the analyzing part 10 has been subjected to a surface treatment having a water-repellent property to the measurement object liquid. As an example of such a surface treatment, application of a fluororesin onto the region 10b can be mentioned. The region 10b may be only the surroundings of the analyzing part 10, or may be the whole surface of the microchip except the analyzing part 10.

Figure 9:
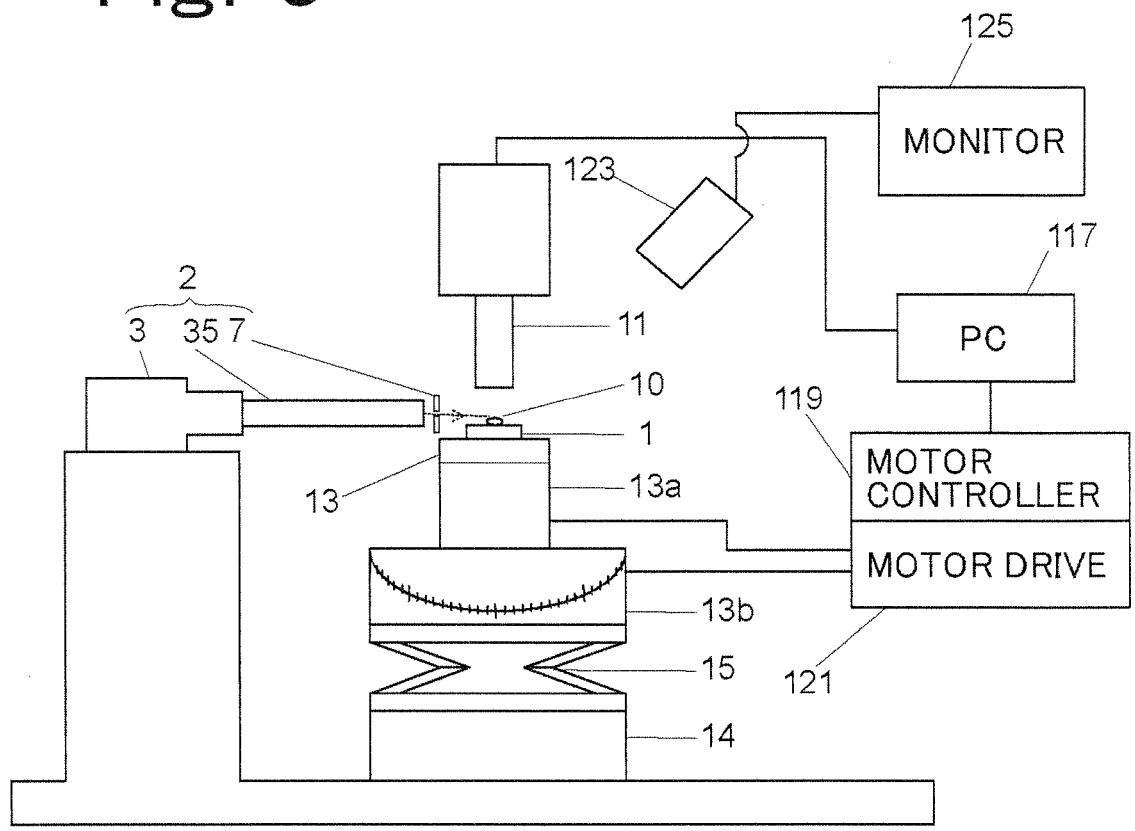
FIG. 9 is a schematic front view showing another embodiment of an analyzing device.
Figure 10A:
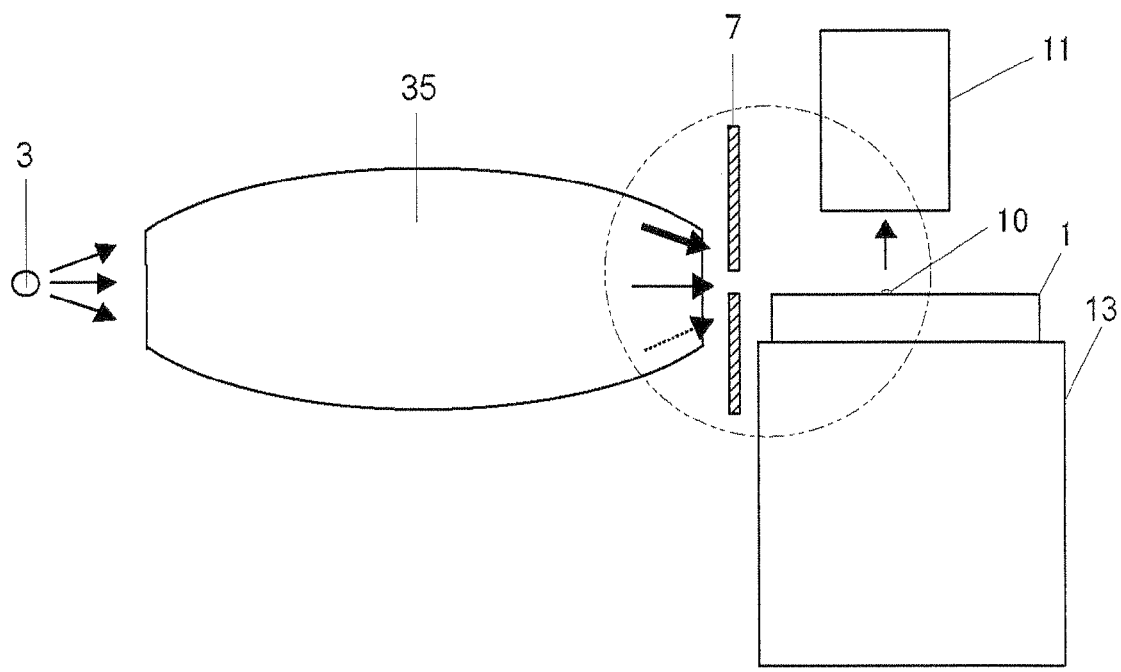
FIG. 10A is a cross-sectional front view showing an arrangement of a polycapillary X-ray lens and a slit in the analyzing device of the embodiment.
Figure 10B:
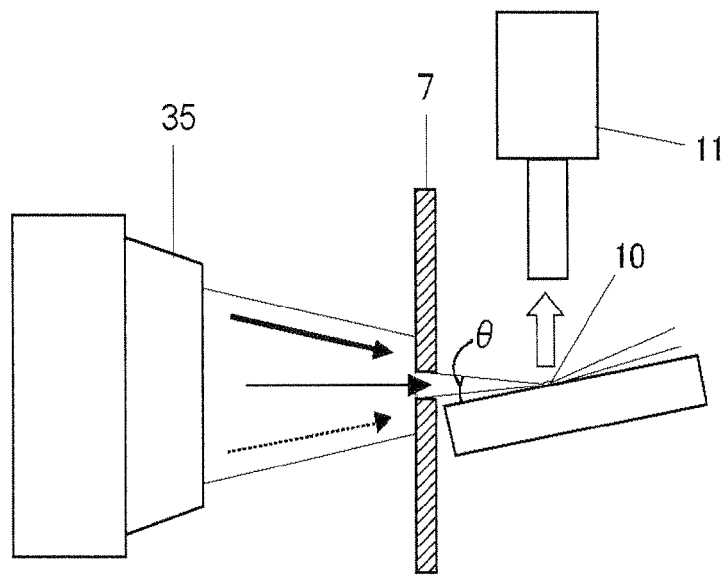
FIG. 10B is an enlarged view of a part enclosed with a chain-line circle in FIG. 10A.
Figure 11A:
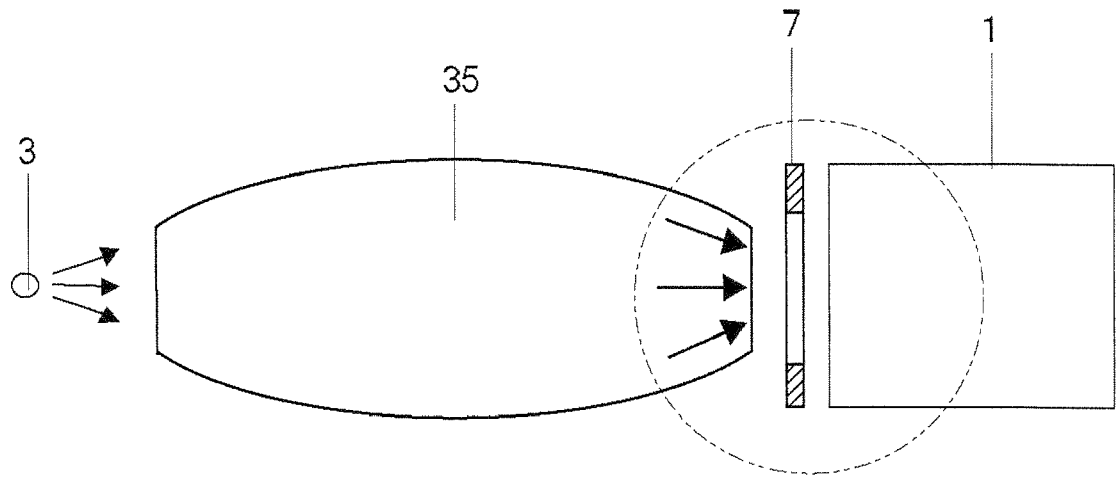
FIG. 11A is a cross-sectional top view showing an arrangement of a polycapillary X-ray lens and a slit in the analyzing device of the embodiment.
Figure 11B:
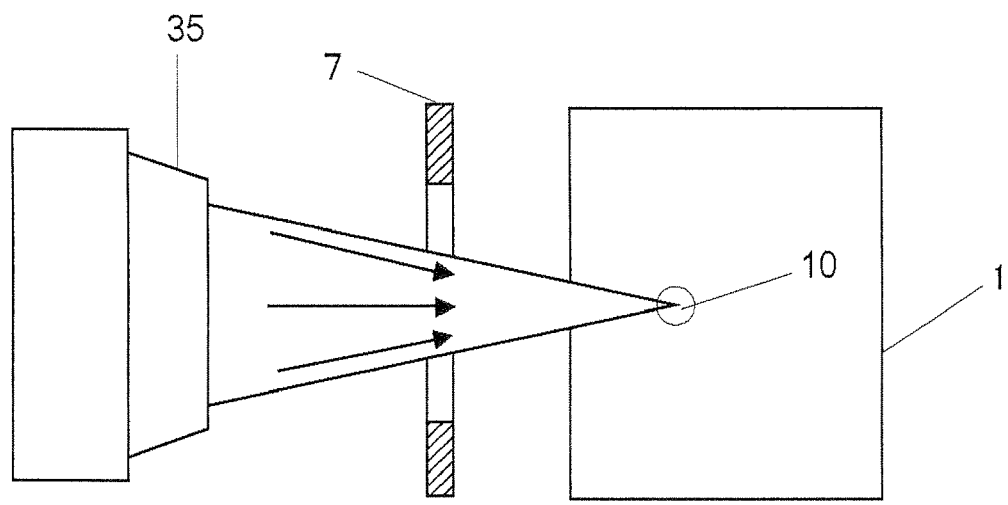
FIG. 11B is an enlarged view of a part enclosed with a chain-line circle in FIG. 11A.

FIG. 9 is a schematic front view of another embodiment of the analyzing device using this microchip. FIGS. 10A and 11A are a cross-sectional front view and a cross-sectional top view showing the arrangement of a polycapillary X-ray lens 35 and a slit 7. In each drawing, FIGS. 10B and 11B are enlarged views of the parts encircled with the chain line in FIGS. 10A and 11A.

The primary X-ray radiating part 2 that makes a primary X-ray enter the surface of the sample 1 mounted on the sample mounting base 13 at an angle of entering that provokes total reflection includes an X-ray source 3 for generating the primary X-ray and a polycapillary X-ray lens 35 for condensing and radiating the primary X-ray onto the sample 1. The primary X-ray can be condensed to have a beam diameter of several tens of micrometers with use of the polycapillary X-ray lens 35.

The polycapillary X-ray lens 35 has a structure consisting of a bundle of numerous monocapillaries. In the drawings, illustration of individual monocapillaries is omitted. The monocapillary is a quartz tube having an inner diameter of several microns. The monocapillary has such a shape that the inner diameter thereof enlarges once from the base end on the photoreceptive part side towards the tip end on the radiation side, and then gradually narrows towards the tip end.

This embodiment is further provided with a slit 7 parallel to the substrate 1 in order to shield against the primary X-ray having an angle of entering that does not satisfy the conditions of total reflection relative to the surface of the microchip 1 among the primary X-rays exiting from the polycapillary X-ray lens 35. In order to detect the fluorescent X-ray generated from the microchip 1, a detector 11 is disposed opposite to the surface of the microchip 1 mounted on the sample mounting base 13.

The sample mounting base 13 is provided with adjustment mechanisms 13a, 13b for adjusting the directions in a horizontal plane and the height direction of the surface of the microchip 1 mounted thereon and the inclination direction of the surface of the microchip 1 relative to the entering X-ray. The analyzing part 10 which is the measurement site on the surface of the microchip 1 is located immediately below the detector 11, whereby the angle of entering of the entering X-ray can be adjusted. The sample mounting base 13 is mounted on a manually movable X-Y stage 14 that is movable in the directions (X-Y directions) in the horizontal plane via a manually operated jack 15 that adjusts the height direction (Z-direction). The adjustment mechanisms 13a, 13b of the sample mounting base 13 includes an X-Y-Z stepping motor 13a for adjusting the directions in a horizontal plane and the height direction (X-Y-Z direction) of the surface of the microchip 1 by mounting the microchip 1 on the top surface thereof and an inclination motor 13b that is disposed under the X-Y-Z stepping motor 13a for adjusting the inclination direction of the surface of the microchip 1 relative to the entering X-ray. The sample mounting base 13 supports the microchip 1 mounted thereon and enables the movement in the X, Y, Z directions as well as the rotational movement that inclines the sample surface.

The X-Y-Z stepping motor 13a and the inclination motor 13b are driven by a motor drive 121, and the motor drive 121 is controlled by a motor controller 119 that is controlled by a personal computer (PC) 117.

In order to monitor the surface of the microchip 1 so that the analyzing part 10 of the measurement site on the surface of the microchip 1 mounted on the sample mounting base 13 will be located at the rotational center of the inclination motor 13b and at the focal position of the primary X-ray provided by the polycapillary X-ray lens 35, a CCD camera 123 is disposed to be located obliquely above the sample mounting base 13, and images of the surface state of the microchip 1 captured by the CCD camera 123 are displayed on a monitor 125.

The adjustment of the focal position of the polycapillary X-ray lens 35 by the CCD camera 123 is carried out as follows. First, a tungsten (W) wire having a diameter of about 10 μm is attached in a cross shape onto the surface of the sample mounting base 13 or the flat substrate mounted thereon, and this is regarded as a sample. The cross-shaped tungsten wire is roughly positioned at a position that is assumed to be the focal position of the polycapillary X-ray lens 35 by the manually movable X-Y stage 14 and the manually operated jack 15.

Next, an X-ray is radiated from the X-ray source 3 and, while monitoring the fluorescent X-ray coming from the cross-shaped tungsten wire, the X-Y-Z stepping motor 13a is driven to search for the position of the X-ray beam. That is, the position that attains the maximum detection intensity of the fluorescent X-ray is the focal position of the polycapillary X-ray lens 35. When the focal position of the polycapillary X-ray lens 35 is determined, the position of the CCD camera 123 and the focus thereof are adjusted so that the focus of the CCD camera 123 will come to the position of the cross-shaped tungsten wire at that time. That is, from the next time on, the position at which the CCD camera 123 is focused while looking at the monitor 125 will be the focal position of the X-ray beam by the polycapillary X-ray lens 35.

As the X-ray source 3, a commercially available X-ray tube is used. An X-ray transmitting material such as beryllium, boron nitride, or graphite is used for the X-ray exiting window of the X-ray source 3. Between the X-ray exiting window of the X-ray source 3 and the polycapillary X-ray lens 35, there may be provided a suitable filter such as a zirconium, aluminum, or brass filter in accordance with the elements to be measured so as to prevent the X-ray deriving from the tube bulb from affecting the fluorescent X-ray measurement. Here, as the X-ray source 3, an X-ray tube was used having molybdenum as a target and having a beryllium X-ray exiting window. A zirconium filter was disposed between the X-ray exiting window of the X-ray source 3 and the polycapillary X-ray lens 35.

As shown in FIGS. 10A and 10B, the X-ray generated from the X-ray source 3 is condensed three-dimensionally in a spot-like manner to a minute region in the analyzing part 10 on the surface of the microchip 1 by the polycapillary X-ray lens 35, thereby generating an optical path of the primary X-ray that enters at a larger angle of entering than the critical angle of total reflection relative to the flat surface of the microchip 1. The opening 9c that will be an outlet of the sample liquid is present within the region of the analyzing part 10. The position at which the X-ray is condensed is placed at a position that evades the opening 9c. So that the position at which the X-ray is condensed will not overlap the opening 9c, the region of the analyzing part 10 is determined so that the opening 9c will evade the central part of the region of the analyzing part 10 and will preferably come to the surrounding part.

As shown in FIG. 10B, the slit 7 disposed between the polycapillary X-ray lens 35 and the microchip 1 shields against the X-rays having an angle θ of entering that exceeds the critical angle $θ_0$ of the total reflection among the primary X-rays entering the surface of the microchip 1.

For the X-ray detector, one is provided with a wavelength dispersive spectrometer and another is provided with an energy dispersive X-ray spectrometer. The wavelength dispersive spectrometer uses a diffraction phenomenon of a crystal of warpage type. The energy dispersive X-ray spectrometer captures all the X-rays generated from the sample simultaneously into the detector, and performs energy selection of the X-rays in an electrical manner. The energy dispersive X-ray spectrometer has an advantage in that, though the energy dissolution performance is inferior to that of the wavelength dispersive spectrometer, the measurement time can be made short, and the whole energy range can be simultaneously measured. In contrast, the wavelength dispersive spectrometer has an advantage in that, though the measurement time will be longer than that of the energy dispersive X-ray spectrometer, the energy dissolution performance is superior. In the element analysis, either one of these two kinds of spectrometers different in dissolution performance can be used, and also these may be used in combination. Here, in order to make the measurement time short, an energy dispersive X-ray spectrometer is used.

Hereafter, in order to see the performance of the device of this embodiment, a silicon wafer is disposed in place of the microchip 1, and the measurement is carried out. The silicon wafer is regarded as the sample 1. The sample 1 is mounted on the sample mounting base 13, and while looking at the surface images of the sample 1 displayed on the monitor 125, the manually movable X-Y stage 14 and the manually operated jack 15 are adjusted so that the measurement site of the surface of the sample 1 will come to the rotational center of the inclination motor 13b and at the focal position of the primary X-ray provided by the polycapillary X-ray lens 35. That is, since the CCD camera 123 is adjusted in advance so as to be focused to the focal position of the X-ray beam provided by the polycapillary X-ray lens 35, the manually movable X-Y stage 14 and the manually operated jack 15 are adjusted so that the surface images of the sample 1 displayed on the monitor 125 will be in a state of being focused.

Next, while radiating an X-ray to the sample 1 from the X-ray source 3, the fluorescent X-ray is captured by the X-ray detector 11, and the X-Y-Z stepping motor 13a and the inclination motor 13b are adjusted by the intensity thereof, so as to perform fine adjustment of the X, Y, Z directions and the inclination angle of the surface of the sample 1. As the X-ray source 3, an Mo target was operated at 50 keV, 0.5 mA.

As the slit 7, one having an elongate opening parallel to the surface of the sample 1 and having a width of 30 µm is disposed. For adjustment of the height thereof, the intensity of the SiKα line which is the fluorescent X-ray from the silicon wafer serving as the sample 1 is monitored while moving the slit 7 in an up-and-down direction, and the slit 7 is set at the position that attains the maximum intensity thereof. FIG. 12 is the result of the monitoring of the intensity of the SiKα line. In this example, the slit 7 was adjusted to be at the center of the exit of the polycapillary X-ray lens 35 at the position at which the slit 7 was moved upwards by about 2 mm from the standard position at which the slit 7 was placed, whereby the maximum intensity was obtained. The vertical axis of FIG. 12 represents the integrated value of the detected value for 60 seconds, and the numerical values on the horizontal axis are for this embodiment, so that the numerical values themselves do not have a universal meaning.

Figure 13:
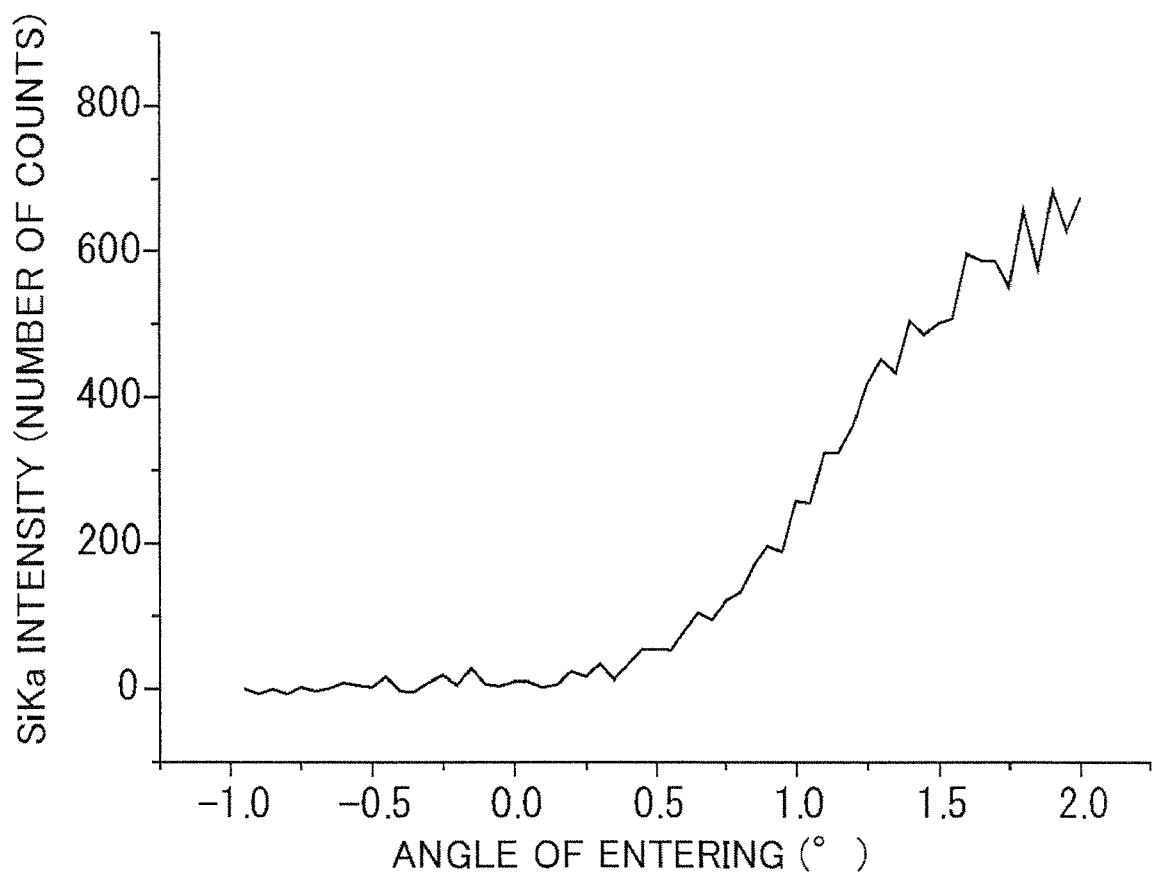
FIG. 13 is a graph showing a relationship between an angle of entering of an X-ray beam and an intensity of a SiKα line, which is a fluorescent X-ray from a silicon wafer, in the analyzing device of the embodiment.

In FIG. 13, after the height of the slit 7 is adjusted to an optimum position (in this case, the position having a height of about 2 mm) as shown in FIG. 12, the inclination motor 13b is driven to change the inclination of the surface of the sample 1, whereby the angle of entering of the X-ray beam relative to the surface of the sample 1 is changed, so as to monitor the SiKα line intensity. The vertical axis of FIG. 13 is an integrated value of the detected value for 60 seconds, and the horizontal axis represents read values of the inclination motor 13b which is an inclined stage. Since the raising of the intensity is observed around about 1.0 degree, the position around there seems to be the critical angle of total reflection in the device of this embodiment.

Figure 14:
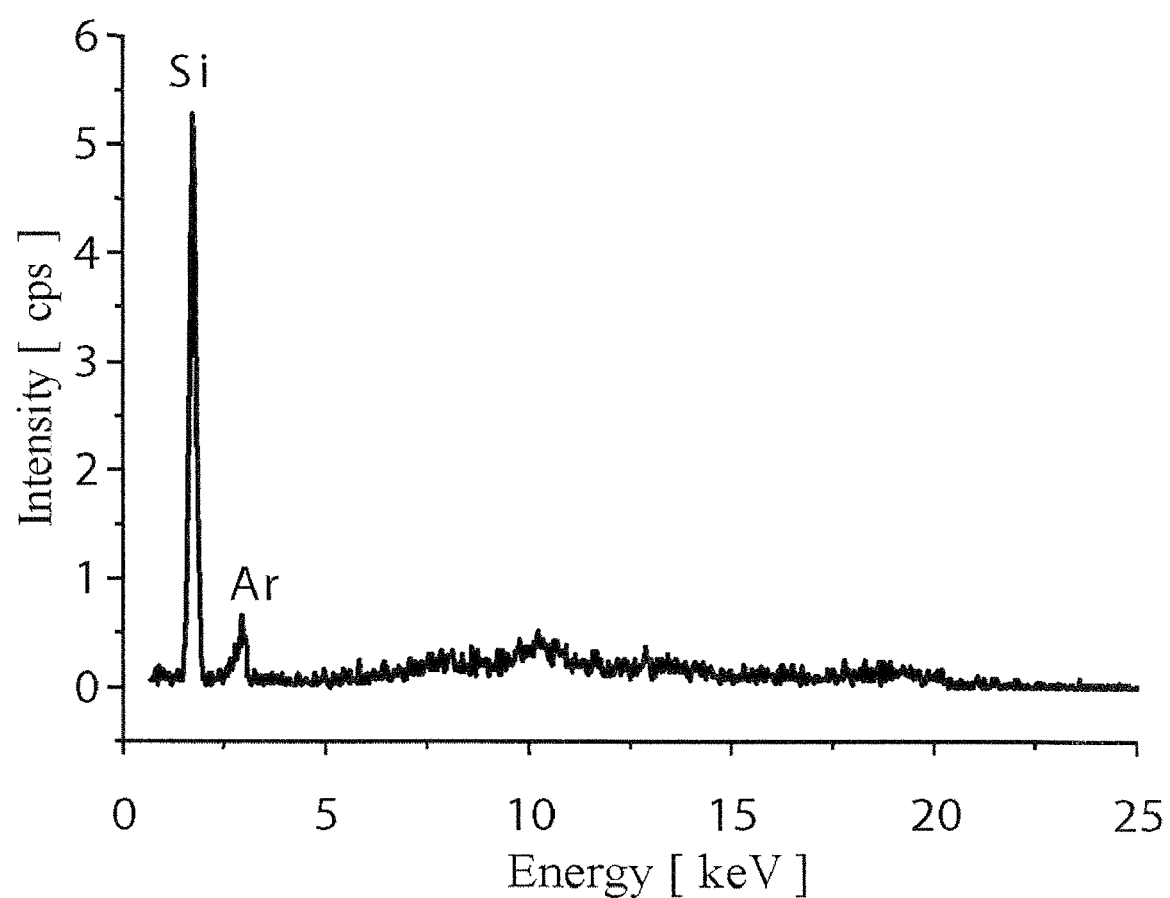
FIG. 14 is a fluorescent X-ray spectrum of a silicon wafer as measured by the analyzing device of the embodiment.

FIG. 14 shows a fluorescent X-ray spectrum of the silicon wafer obtained under the conditions adjusted in this manner. The vertical axis shows the fluorescent X-ray intensity as an average value per one second (counts/second). This fluorescent X-ray spectrum is obtained when the inclination of the sample is set to be 1.0 degree (FIG. 13) as a read value of the inclination motor 13b and the Mo target of the X-ray source 3 is operated at 50 keV, 0.5 mA. A distinct fluorescent X-ray of Si has been detected. Although the fluorescent X-ray of Ar is also detected, this Ar seems to be due to excitation of Ar in ambient atmosphere near the silicon wafer or in the X-ray optical path.

Figure 15:
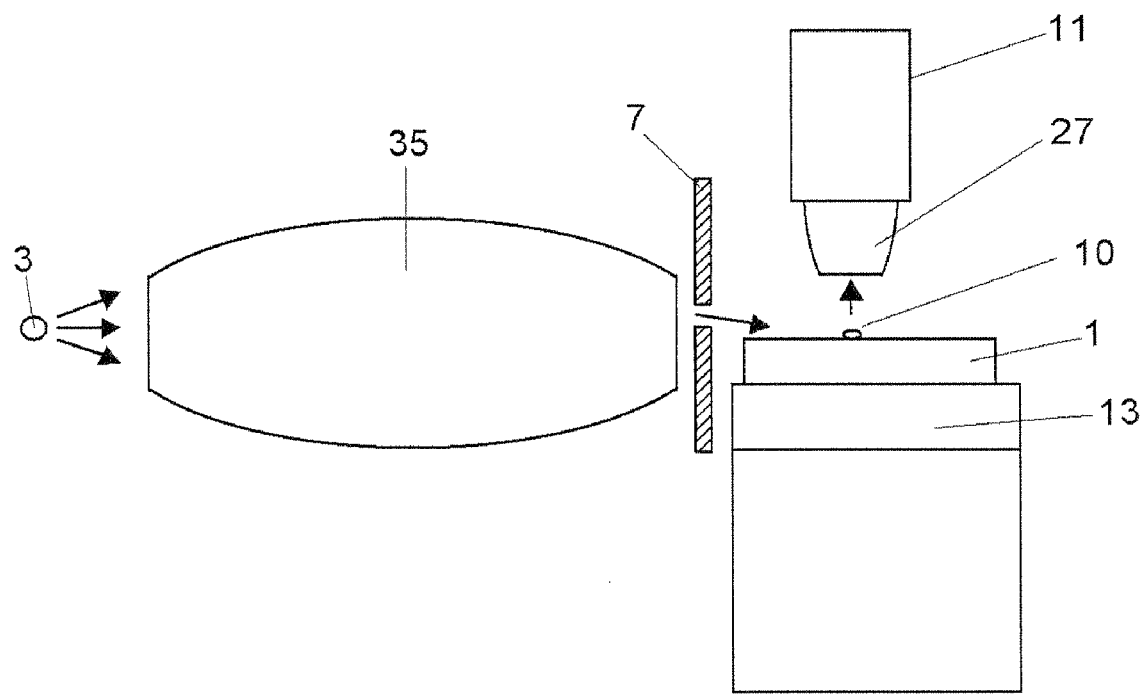
FIG. 15 is a schematic cross-sectional front view showing an essential part of still another embodiment of the analyzing device.

FIG. 15 is a schematic front view of still another embodiment of the analyzing device using this microchip. A polycapillary X-ray lens 27 is mounted also on the detector side that receives the fluorescent X-ray coming from the analyzing part 10 of the microchip 1. The construction other than the polycapillary X-ray lens 27 is the same as in the embodiment of FIG. 9.

By mounting the polycapillary X-ray lens 27 also on the detector side, the signal from the minute part can be detected with good efficiency, thereby improving not only the detection efficiency but also the S/B (signal to background) ratio because the signals of the X-rays other than those coming from the minute part sample will not be captured.

Figure 16A:
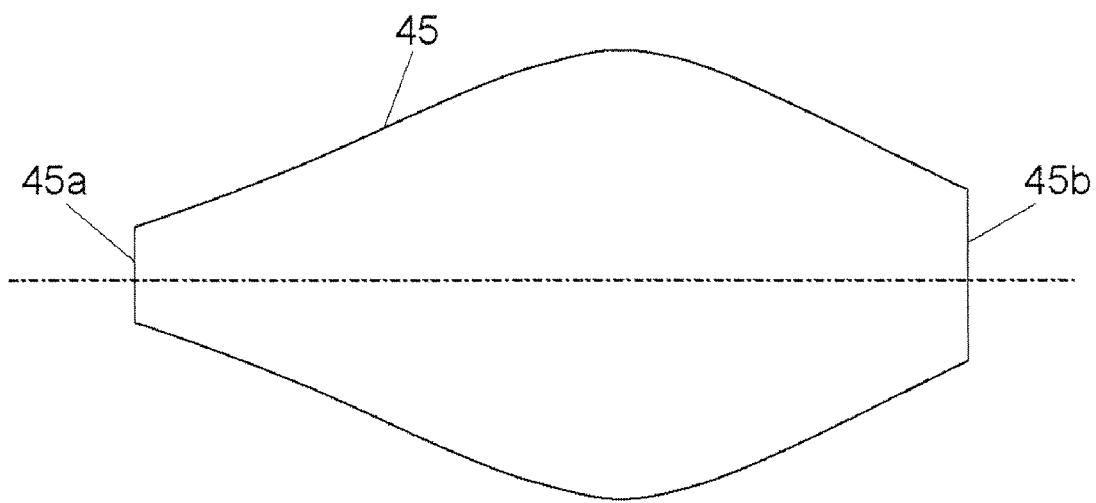
FIG. 16A is a plan view representing another example of a polycapillary X-ray lens on a primary X-ray radiation side.
Figure 16B:
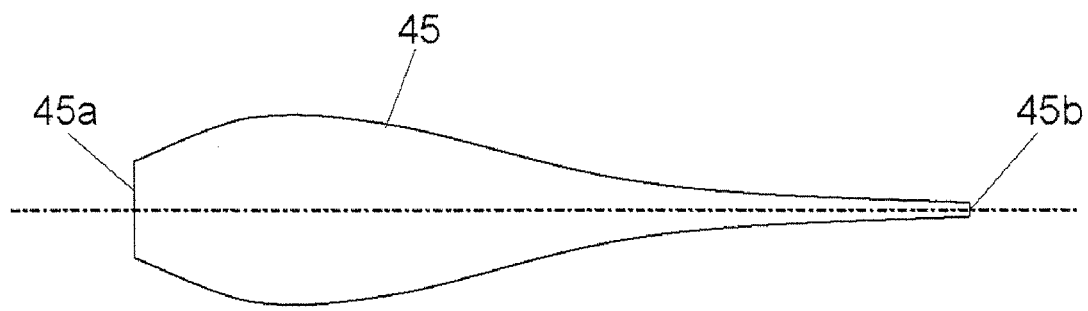
FIG. 16B is a side view of the polycapillary X-ray lens.
Figure 17:
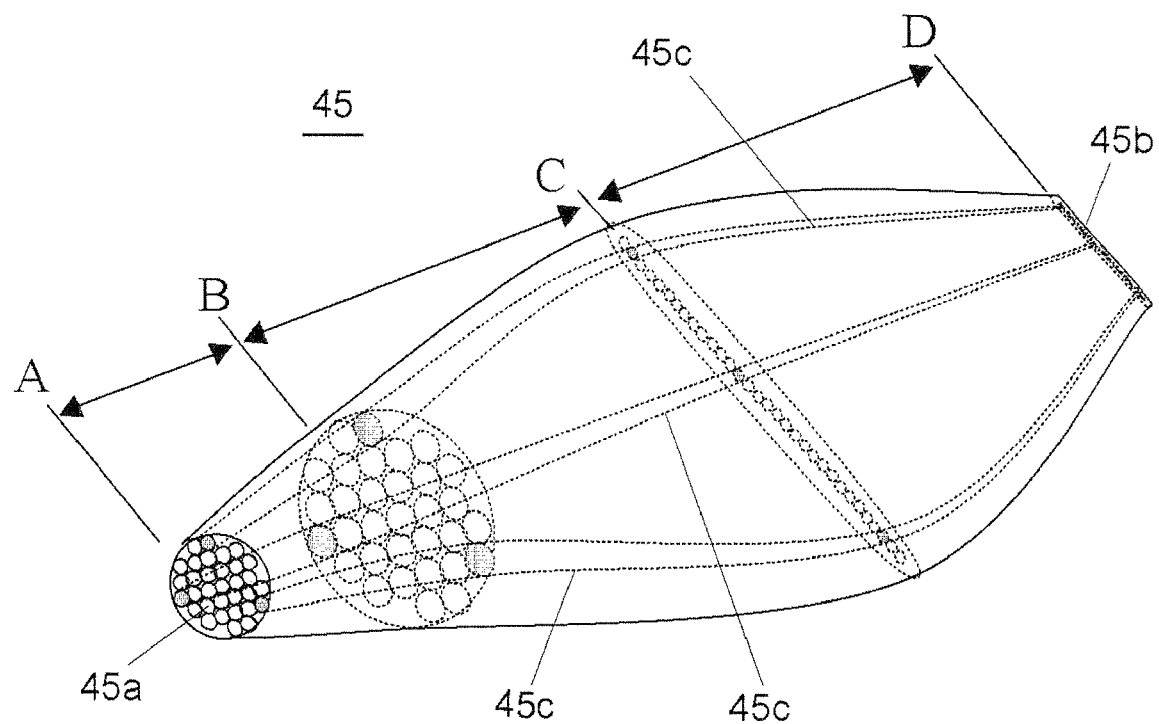
FIG. 17 is a perspective view of the polycapillary X-ray lens.

FIGS. 16A, 16B, and 17 show another embodiment of the polycapillary X-ray lens on the primary X-ray radiation side. FIG. 16A is a plan view; FIG. 16B is a side view; and FIG. 17 is a perspective view of the polycapillary X-ray lens schematically showing an arrangement of the monocapillaries.

A polycapillary X-ray lens 45 is a bundle of numerous monocapillaries 45c as shown in FIG. 17. In FIGS. 16A and 16B, illustration of individual monocapillaries is omitted. The monocapillaries 45c are the same as those constituting the polycapillary X-ray lens 35 shown in FIGS. 10A and 10B; however, the way of bundling is different.

In the polycapillary X-ray lens 45, a plane 45a of entering facing the X-ray has a circular shape. The plane 45a receives radiation of the stereoscopic X-ray coming from the X-ray source serving as a point light source. So that the X-ray entering each monocapillary 45c whose end surface is disposed at the plane 45a of entering may be propagated to a plane 45b of exiting while being subjected to total reflection by each monocapillary 45c, the inner diameter of each monocapillary 45c enlarges from the A part on the entering side towards the B part. Further, between B-C at the middle part, the monocapillaries are rearranged by changing from the plane arrangement to the straight-line arrangement. Further, between C-D on the exiting side, the monocapillaries are arranged to fix the focus so that the directions of exiting will be concentrated into one point. The analyzing part of the microchip is disposed at the position that will be the focus. Also, between C-D, the inner diameter of the monocapillaries gradually decreases.

With such a structure, at the plane 45a of entering of the polycapillary X-ray lens opposing the X-ray source, end parts of the plurality of monocapillaries 45c are arranged to form a planar shape, so that almost the total amount of the X-rays stereoscopically radiated from the X-ray source is captured into the polycapillary X-ray lens 45. The X-rays captured into the polycapillary X-ray lens 45 repeat total reflection on the inner wall of each monocapillary 45c, and propagate through the monocapillary 45c having an inner diameter that widens once from the plane of entering towards the plane of exiting and then gradually narrows, so as to reach the plane 45b of exiting of the polycapillary X-ray lens that faces the analyzing part of the microchip. At the plane 45b of exiting, end parts of the plurality of monocapillaries are arranged in a linear form parallel to the microchip surface so as to achieve the same angle of total reflection relative to the microchip surface of the analyzing part. Also, in the horizontal directions, the monocapillaries 45c are arranged so that the radiation direction of each monocapillary 45c is directed to be concentrated to the position at which the sample is placed.

Figure 18:
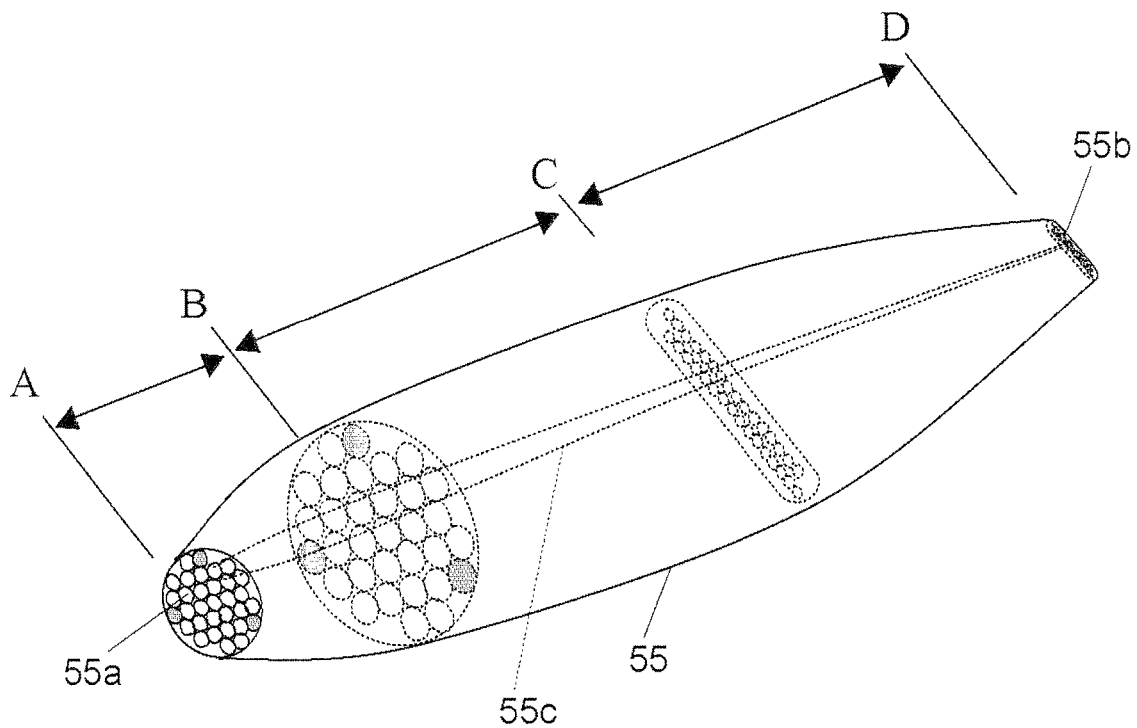
FIG. 18 is a perspective view representing still another example of a polycapillary X-ray lens on the primary X-ray radiation side.

FIG. 18 shows still another embodiment of the polycapillary X-ray lens on the primary X-ray radiation side, and is a perspective view of the polycapillary X-ray lens schematically showing the arrangement of the monocapillaries. As shown in FIG. 18, when the monocapillaries of a plane 55b of exiting are arranged in two rows or in a plurality of rows in a vertical direction within a range in which the conditions of total reflection are not considerably changed, a polycapillary X-ray lens 55 can be advantageously reduced in scale. At a plane 55a of entering of the polycapillary X-ray lens that faces the X-ray source, end parts of a plurality of monocapillaries 55c are arranged in a plane form.

Figure 19:
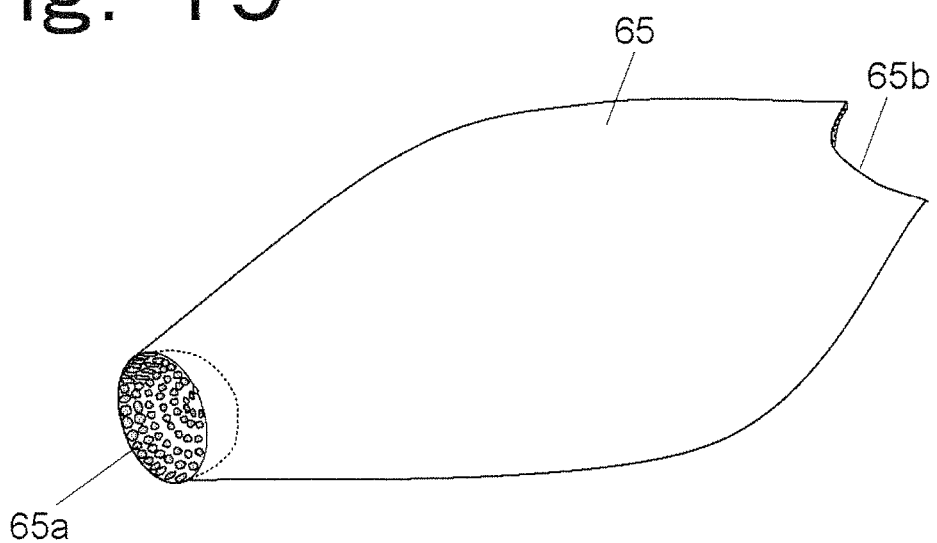
FIG. 19 is a perspective view representing still another example of a polycapillary X-ray lens on the primary X-ray radiation side.

FIG. 19 is a perspective view showing still another embodiment of the polycapillary X-ray lens on the primary X-ray radiation side. As shown in FIG. 19, a plane 65a of entering is made spherical so as to facilitate photoreception of the exiting X-ray coming from the X-ray source. Also, planes 65b of exiting are arranged in a curved line shape as viewed from above, so as to enhance the degree of condensation of the exiting X-ray. The polycapillary X-ray lens such as this is advantageous in achieving scale reduction.

The polycapillary X-ray lens is fabricated by heating and stretching a bundle of monocapillary source materials having the maximum diameter (for example, the B part of FIGS. 17 and 18). The diameter is reduced by pulling in the A part (see FIGS. 17 and 18) direction. In the C-D direction (see FIGS. 17 and 18), the monocapillaries are stretched while restraining the arrangement in a plane shape, so as to achieve an arrangement in which the monocapillaries converge in a fan shape.

The present invention is not limited to the above-described embodiments alone, so that it can be implemented within the range as recited in the claims. For example, in the above-described embodiments, the stepping motor 13a and the inclination motor 13b were used as an adjustment mechanism for adjusting the angle of entering of the primary X-ray. However, it can also be adjusted so that the primary X-ray may satisfy the conditions of total reflection on the microchip by adjusting the X-ray radiation part 2. Alternatively, it can also be adjusted so that the primary X-ray may satisfy the conditions of total reflection on the microchip by adjusting both the X-ray radiation part 2 and the stepping motor 13a and the inclination motor 13b.

INDUSTRIAL APPLICABILITY

The present invention can be used in instrumental analyzing devices that deal with reaction, separation and the like of an extremely small amount of solution using a microchip and detects the result thereof.

What is claimed is:

1. A microchip for analyzing a total reflection fluorescent X-ray, comprising:
    a substrate;
    a channel formed in the substrate; and
    an analyzing part consisting of a partial region of a flat surface of the substrate and including an outlet of the channel, wherein the outlet is formed as an opening within the flat surface of the substrate, and a measurement object liquid overflowed from the opening stays on the flat surface of the substrate to become a sample of analysis,
    wherein the analyzing part is defined by surroundings thereof subjected to a water-repellent surface treatment with fluororesin, has a circular or elliptic shape, and has a size configured to make a primary X-ray enter under total reflection conditions, and does not have undulations obstructing the total reflection within a region forming the analyzing part, and
    the outlet is disposed at a position offset from a center of the region.

2. The microchip according to claim 1, wherein the analyzing part is subjected to a surface treatment having affinity to the measurement object liquid.

3. The microchip according to claim 1, wherein the analyzing part has a circular shape having an area of 20 to 80 $mm^2$.

4. A total reflection fluorescent X-ray analyzing method using the microchip according to claim 1 and comprising the following steps (A) to (C):
    (A) step of making the measurement object liquid overflow as a sample of analysis from the channel through the opening to the analyzing pad and thereafter drying the sample of analysis;
    (B) step of making a primary X-ray enter the sample of analysis overflowed to the analyzing pad so as to achieve conditions of total reflection relative to a surface of the microchip at a position that evades the opening within the analyzing pad; and
    (C) step of detecting a fluorescent X-ray generating from the sample of analysis.

5. The total reflection fluorescent X-ray analyzing method according to claim 4, wherein at least one of liquid-supplying, chemical reaction and separation is carried out in the channel.

6. The total reflection fluorescent X-ray analyzing method according to claim 4, wherein the primary X-ray radiated onto the sample of analysis is condensed with use of a polycapillary X-ray lens in the step (B).

7. The total reflection fluorescent X-ray analyzing method according to claim 6, wherein the primary X-ray exiting from the polycapillary X-ray lens is such that a cross-sectional shape in a direction perpendicular to a propagation direction is a linear shape parallel to the microchip surface.

8. The total reflection fluorescent X-ray analyzing method according to claim 6, wherein a primary X-ray part having an angle of entering that does not satisfy total reflection conditions relative to the microchip surface among the primary X-rays radiated onto the sample of analysis is shielded.

9. The total reflection fluorescent X-ray analyzing method according to claim 4, wherein a polycapillary X-ray lens is disposed also on a side of the detector that detects the fluorescent X-ray so as to detect only the fluorescent X-ray coming from a minute region of the sample of analysis.

10. A microchip analyzing device using the microchip according to claim 1, as a medium of measurement and comprising:
    a sample mounting base for mounting the microchip;
    an X-ray source for generating a primary X-ray;
    a primary X-ray entering adjustment mechanism for making the primary X-ray enter the analyzing part of the microchip mounted on the sample mounting base under conditions of total reflection; and an X-ray detector disposed opposite to the analyzing part of the microchip for detecting a fluorescent X-ray generating from a sample of analysis on the analyzing part, wherein the primary X-ray entering adjustment mechanism includes a polycapillary X-ray lens for condensing and radiating the primary X-ray onto the microchip mounted on the sample mounting base, the polycapillary X-ray lens is a bundle of numerous monocapillaries, and each monocapillary has such a shape that an inner diameter thereof once enlarges from a base end on a photoreceptive part side to a tip end on a radiation side and then gradually narrows toward the tip end, the polycapillary X-ray lens is such that end parts of the monocapillaries on a plane of entering opposite to an X-ray emission source are arranged in a circular plane shape, and end parts of the monocapillaries on a plane of exiting opposite to the sample are arranged to have a linear shape parallel to a surface of the microchip mounted on the sample mounting base so that radiation directions may be condensed towards one point, and the sample mounting base and the primary X-ray entering adjustment mechanism are adjusted so that the primary X-ray may enter a position that evades the opening within the analyzing part of the microchip.

11. The microchip analyzing device according to claim 10, wherein the primary X-ray entering adjustment mechanism comprises a slit between an exiting side of the polycapillary X-ray lens and the sample mounting base, and the slit is disposed to shield against the primary X-ray having an angle of entering that does not satisfy total reflection conditions relative to a surface of the microchip mounted on the sample mounting base.

12. The microchip analyzing device according to claim 10, wherein the sample mounting base comprises an adjustment mechanism for adjusting directions in a horizontal plane, a height direction, and an inclination direction relative to an entering X-ray, of a surface of the microchip mounted thereon.

13. The microchip analyzing device according to claim 10, comprising a polycapillary X-ray lens between the microchip mounted on the sample mounting base and the detector so as to detect only the fluorescent X-ray coming from a minute region within the analyzing part.

* * * * *